US007167757B2

(12) United States Patent
Ingle et al.

(10) Patent No.: US 7,167,757 B2
(45) Date of Patent: Jan. 23, 2007

(54) ENERGY INDUCED BULKING AND BUTTRESSING OF TISSUE FOR INCONTINENCE

(75) Inventors: Frank W. Ingle, Palo Alto, CA (US); Garry L. Carter, Pleasanton, CA (US); Michael D. Laufer, Menlo Park, CA (US)

(73) Assignee: AMS Research Corporation, Minneapolis, MN (US)

( * ) Notice: Subject to any disclaimer, the term of this patent is extended or adjusted under 35 U.S.C. 154(b) by 47 days.

(21) Appl. No.: 10/827,887

(22) Filed: Apr. 19, 2004

(65) Prior Publication Data
US 2004/0236393 A1 Nov. 25, 2004

Related U.S. Application Data

(60) Continuation of application No. 09/946,907, filed on Sep. 4, 2001, now Pat. No. 6,836,688, which is a continuation of application No. 09/441,109, filed on Nov. 16, 1999, now Pat. No. 6,772,013, which is a division of application No. 08/910,370, filed on Aug. 13, 1997, now Pat. No. 6,091,995, which is a continuation-in-part of application No. 08/862,875, filed on May 23, 1997, now abandoned, which is a continuation-in-part of application No. 08/748,527, filed on Nov. 8, 1996, now abandoned.

(51) Int. Cl.
*A61F 7/12* (2006.01)
(52) U.S. Cl. .................. 607/99; 607/101; 607/102; 607/113
(58) Field of Classification Search .................. 606/41, 606/42, 45, 46, 48–50; 607/101, 102, 133, 607/138, 113; 128/898
See application file for complete search history.

(56) References Cited

U.S. PATENT DOCUMENTS 373,399 A 11/1887 Hamilton (Continued)

FOREIGN PATENT DOCUMENTS

WO WO 93/07815 A1 4/1993

(Continued)

OTHER PUBLICATIONS

Benson, Thomas, J., Female Pelvic Floor Disorders: Investigation and Management, Norton Medical Books, W.W. Norton & Company, New York, New York, 1992, pp. 239-240.

(Continued)

*Primary Examiner*—Roy D. Gibson
(74) *Attorney, Agent, or Firm*—Barbara A. Wrigley; Oppenheimer Wolff & Donnelly LLP; Jose' W. Jimenez

(57) ABSTRACT

Devices, systems, and method for treating urinary incontinence generally rely on energy delivered to a patient's own pelvic support tissue to selectively contract or shrink at least a portion of that pelvic support tissue so as to reposition the bladder. Devices and methods apply gentle resistive heating of tissues to cause them to contract without imposing significant injury on the surrounding tissue structures. Alternative heat-applying probes heat tissue structures which comprise or support a patient's urethra. By selectively contracting the support tissues, the bladder neck, sphincter, and other components of the urinary tract responsible for the control of urinary flow can be reconfigured or supported in a manner which reduces urinary leakage.

11 Claims, 22 Drawing Sheets

U.S. PATENT DOCUMENTS

| | | |
|---|---|---|
| 3,575,158 A | 4/1971 | Summers |
| 3,749,098 A | 7/1973 | De Bennetot |
| 3,924,631 A | 12/1975 | Mancusi, Jr. |
| 3,926,175 A | 12/1975 | Allen et al. |
| 3,939,821 A | 2/1976 | Roth |
| 4,311,145 A | 1/1982 | Esty et al. |
| 4,326,529 A | 4/1982 | Doss et al. |
| 4,409,453 A | 10/1983 | Smith |
| 4,453,536 A | 6/1984 | Abild |
| 4,686,962 A | 8/1987 | Haber |
| 4,765,331 A | 8/1988 | Petruzzi et al. |
| 4,773,393 A | 9/1988 | Haber et al. |
| 4,776,344 A | 10/1988 | Shirasaki et al. |
| 4,802,479 A | 2/1989 | Haber et al. |
| 4,807,620 A | 2/1989 | Strul et al. |
| 4,832,680 A | 5/1989 | Haber et al. |
| 4,994,019 A | 2/1991 | Fernandez et al. |
| 5,012,822 A | 5/1991 | Schwarz |
| 5,035,696 A | 7/1991 | Rydell |
| 5,041,109 A | 8/1991 | Abela |
| 5,057,106 A | 10/1991 | Kasevich et al. |
| 5,098,429 A | 3/1992 | Sterzer |
| 5,103,804 A | 4/1992 | Abele et al. |
| 5,140,999 A | 8/1992 | Ardito |
| 5,190,517 A | 3/1993 | Zieve et al. |
| 5,201,732 A | 4/1993 | Parins et al. |
| 5,213,097 A | 5/1993 | Zeindler |
| 5,230,334 A | 7/1993 | Klopotek |
| 5,234,409 A | 8/1993 | Goldberg et al. |
| 5,256,133 A | 10/1993 | Spitz |
| 5,281,217 A | 1/1994 | Edwards et al. |
| 5,281,218 A | 1/1994 | Imran |
| 5,282,799 A | 2/1994 | Rydell |
| 5,293,869 A | 3/1994 | Edwards et al. |
| 5,304,123 A | 4/1994 | Atala et al. |
| 5,309,910 A | 5/1994 | Edwards et al. |
| 5,314,465 A | 5/1994 | Maurer et al. |
| 5,314,466 A | 5/1994 | Stern et al. |
| 5,366,490 A | 11/1994 | Edwards et al. |
| 5,370,671 A | 12/1994 | Maurer et al. |
| 5,370,675 A | 12/1994 | Edwards et al. |
| 5,370,677 A | 12/1994 | Rudie et al. |
| 5,370,678 A | 12/1994 | Edwards et al. |
| 5,376,064 A | 12/1994 | Cerny |
| 5,385,544 A | 1/1995 | Edwards et al. |
| 5,403,312 A | 4/1995 | Yates et al. |
| 5,405,346 A | 4/1995 | Grundy et al. |
| 5,411,475 A | 5/1995 | Atala et al. |
| 5,431,649 A | 7/1995 | Mulier et al. |
| 5,437,603 A | 8/1995 | Cerny et al. |
| 5,437,664 A | 8/1995 | Cohen et al. |
| 5,447,529 A | 9/1995 | Marchlinski et al. |
| 5,454,809 A | 10/1995 | Janssen |
| 5,458,596 A | 10/1995 | Lax et al. |
| 5,462,545 A | 10/1995 | Wang et al. |
| 5,496,312 A | 3/1996 | Klicek |
| 5,505,730 A | 4/1996 | Edwards |
| 5,514,130 A | 5/1996 | Baker |
| 5,514,155 A | 5/1996 | Daneshvar |
| 5,533,999 A | 7/1996 | Hood et al. |
| 5,556,396 A | 9/1996 | Cohen et al. |
| 5,558,672 A | 9/1996 | Edwards et al. |
| 5,569,241 A | 10/1996 | Edwards |
| 5,569,242 A | 10/1996 | Lax et al. |
| 5,575,788 A | 11/1996 | Baker et al. |
| 5,588,960 A | 12/1996 | Edwards et al. |
| 5,609,598 A | 3/1997 | Laufer et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,707,367 A | 1/1998 | Nilsson |
| 5,716,385 A | 2/1998 | Mittal et al. |
| 5,728,119 A | 3/1998 | Smith et al. |
| 5,810,847 A | 9/1998 | Laufer et al. |
| 5,954,720 A | 9/1999 | Wilson et al. |
| 5,957,920 A | 9/1999 | Baker |
| 5,964,755 A | 10/1999 | Edwards |
| 6,035,238 A | 3/2000 | Ingle et al. |
| 6,044,846 A | 4/2000 | Edwards |
| 6,056,744 A | 5/2000 | Edwards |
| 6,073,052 A | 6/2000 | Zelickson et al. |
| 6,081,749 A | 6/2000 | Ingle et al. |
| 6,091,995 A | 7/2000 | Ingle et al. |
| 6,169,926 B1 | 1/2001 | Baker |
| 6,197,022 B1 | 3/2001 | Baker et al. |
| 6,228,078 B1 | 5/2001 | Eggers et al. |
| 6,241,753 B1 | 6/2001 | Knowlton |
| 6,277,116 B1 | 8/2001 | Utely et al. |
| 6,480,746 B1 | 11/2002 | Ingle et al. |
| 6,587,731 B1 | 7/2003 | Ingle et al. |

FOREIGN PATENT DOCUMENTS

| | | |
|---|---|---|
| WO | WO 96/00041 A1 | 1/1996 |
| WO | WO 96/00042 A1 | 1/1996 |
| WO | WO 97/15238 A1 | 5/1997 |
| WO | WO 97/32532 A1 | 9/1997 |
| WO | WO 97/39688 A2 | 10/1997 |
| WO | WO 97/43970 A1 | 11/1997 |
| WO | WO 97/43971 A2 | 11/1997 |
| WO | WO 98/07468 A1 | 2/1998 |
| WO | WO 98/38936 A1 | 9/1998 |

OTHER PUBLICATIONS

Finger et al, "Prediction of Transient Temperature Fields and Cumulative Tissue Destruction for Radio Frequency Heating of a Tumor," Medical Physics, University of Texas, Austin Texas; 12 (6) : 1985.

Fulmer, B.R. et al. (2002). "Acute and Long-Term Outcomes of Radio Frequency Bladder Neck Suspension," *The Journal of Urology* 167:141-145.

Hayes et al.; "Prediction of Transient Temperature Fileds and Cumulative Tissue Destruction for Radio Frequency Heating of a Tumor"; 1985, Medical Physics, University of Texas, Austin, Texas, vol. 12, No. 6.

Raz, Shlomo, Female Urology, Second Edition, W.B. Saunders Company, Philadelphia, Pennsylvania, 1996, pp. 126, 340-342, and 356-357.

ENERGY INDUCED BULKING AND BUTTRESSING OF TISSUE FOR INCONTINENCE

CROSS-REFERENCES TO RELATED APPLICATIONS

This application is a continuation of, and claims priority from U.S. patent application Ser. No. 09/946,907 filed on Sep. 4, 2001, now U.S. Pat. No. 6,836,688, which is a continuation of U.S. patent application Ser. No. 09/441,109 filed on Nov. 16, 1999, now U.S. Pat. No. 6,772,013 which is a divisional of U.S. patent application Ser. No. 08/910,370 filed on Aug. 13, 1997, now U.S. Pat. No. 6,091,995; which is a continuation-in-part of U.S. patent application Ser. No. 08/862,875 filed on May 23, 1997 (abandoned); and which is a continuation-in-part of U.S. patent application Ser. No. 08/748,527 filed on Nov. 8, 1996 (abandoned); the full disclosures of which are incorporated herein by reference.

This application is related to U.S. patent applications Ser. No. 08/910,775 filed on Aug. 13, 1997, now U.S. Pat. No. 6,480,746; application Ser. No. 08/910,369 filed on Aug. 13, 1997, now U.S. Pat. No. 6,035,238; and application Ser. No. 08/910,371 filed on Aug. 13, 1997, now U.S. Pat. No. 6,081,749; the full disclosures of which are also incorporated herein by reference.

BACKGROUND OF THE INVENTION

1. Field of the Invention

The present invention generally relates to medical devices, methods, and systems. In a particular aspect, the present invention provides devices, methods, and systems for shrinking tissues, and which are particularly useful for treatment of urinary incontinence in a laparoscopic or minimally invasive manner.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external vaginal sphincter, and most often, the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such non-interventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude the urethra or support the tissues sufficiently to inhibit urinary leakage, but not so much that normal intentional voiding of urine is made difficult or impossible. Balloons and other bulking agents which have been inserted can migrate or be absorbed by the body. The presence of such inserts can also be a source of urinary tract infections.

For these reasons, it would be desirable to provide improved devices, methods, and systems for treating fascia, tendons, and other support tissues which have been strained, or which are otherwise too long to provide the desired support. It would be especially desirable to provide improved methods for treating urinary incontinence in men and women. In particular, it would be desirable to provide methods for treating urinary incontinence in a minimally invasive manner with few or no percutaneous tissue penetrations, preferably utilizing laparoscopic or least invasive manner to minimize patient trauma. It would further be desirable to provide incontinence treatment methods which rely on the existing bladder support structures of the body, rather than depending on the specific length of an artificial support. It would also be desirable to provide methods which rely on introduction of a relatively simple probe into the urethra or vaginal, where tissue structures supporting or comprising the urethra may be caused to partially shrink in order to inhibit urinary leakage.

2. Description of the Background Art

Method and apparatus for controlled contraction of soft tissue are described in U.S. Pat. Nos. 5,569,242, and 5,458, 596. An RF apparatus for controlled depth ablation of soft tissue is described in U.S. Pat. No. 5,514,130.

A bipolar electrosurgical scalpel with paired loop electrodes is described in U.S. Pat. No. 5,282,799. U.S. Pat. No. 5,201,732 describes a bipolar sphincterotomy utilizing side-by-side parallel wires. A disposable electrosurgical instrument is described in U.S. Pat. No. 4,311,145. U.S. Pat. No. 5,496,312, describes an impedance and temperature generator control.

The following patents and published applications relate to the treatment of urinary incontinence. U.S. Pat. Nos. 5,437, 603; 5,411,475; 5,376,064; 5,314,465; 5,304,123; 5,256, 133; 5,234,409; 5,140,999; 5,012,822; 4,994,019; 4,832, 680; 4,802,479; 4,773,393; 4,686,962; 4,453,536; 3,939, 821; 3,926,175; 3,924,631; 3,575,158; 3,749,098; and WO 93/07815.

An electrosurgical probe for the controlled contraction of tissues of the joints and for dermatological indicators is described in U.S. Pat. No. 5,458,596. A bipolar electrosurgical probe having electrodes formed over a restricted arc of its distal end for treatment of, e.g., the esophagus, is described in U.S. Pat. No. 4,765,331. An electrosurgical probe for retrograde sphincterotomy is described in U.S. Pat. No. 5,035,696. Other patents describing electrosurgical probes include U.S. Pat. Nos. 5,462,545; 5,454,809; 5,447, 529; 5,437,664; 5,431,649; 5,405,346; 5,403,312; 5,385, 544; 5,370,678; 5,370,677; 5,370,675; 5,366,490; 5,314, 446; 5,309,910; 5,293,869; 5,281,218; 5,281,217; 5,190, 517; 5,098,429; 5,057,106; 4,807,620; 4,776,344; 4,409, 453; and 373,399.

The disclosure of the present application is related to co-pending U.S. patent application Ser. No. 08/610,911, filed on Mar. 5, 1996, having a common inventor but assigned to a different entity.

SUMMARY OF THE INVENTION

The present invention provides improved devices, methods, and systems for shrinking collagenated tissues, and particularly for treating urinary incontinence. In contrast to prior art methods, the present invention does not rely on implantation of balloons or other materials, nor does it rely on suturing, cutting, or other direct surgical modifications to the genitourinary support tissues. Instead, the present invention relies on delivering energy to a patient's own pelvic support tissue to selectively contract or shrink at least a portion of that pelvic support tissue, thereby raising the position of the bladder. The energy will preferably be applied across bipolar electrodes to the endopelvic fascia and/or the arcus tendineus fascia pelvis. A variety of devices and methods are provided for applying gentle resistive heating to these tissues without significant injury to the support tissues, or to the surrounding tissue structures.

In a first aspect, the present invention provides a probe for heating and contracting fascia. The probe comprises a shaft having a proximal end and a distal end. First and second electrodes are disposed near the distal end of the shaft. These electrodes are simultaneously engageable against the fascia, and are separated by a predetermined distance which limits a depth of tissue heating. A handle is adjacent to the proximal end of the shaft for manipulating the electrodes from outside the patient body.

The bipolar probes of the present invention will generally include a predetermined electrode diameter and electrode separation distance to limit the depth of tissue heating, and will optionally have a temperature sensor mounted between the electrodes. The probe will often be adapted to heat the fascia to temperatures significantly less than most known electrosurgical devices, and may include a control system which limits the total electrical potential applied between the bipolar electrodes to much lower average power levels than known electrosurgical devices. In fact, the present heating probe may be conveniently energized with a battery pack carried in the proximal handle of the probe.

In another aspect, the present invention provides a least invasive probe for heating and contracting fascia of a patient body. The fascia is adjacent to a tissue layer, and the probe comprises a shaft having proximal and distal ends. An electrode is disposed near the distal end of the shaft and is laterally deployable from a narrow configuration to a wide configuration between the fascia and the adjacent tissue layer. The electrode in the wide configuration is exposed to engage the fascia. The electrode in the narrow configuration is disposed along an axis of the shaft to facilitate axial insertion of the probe. A handle is adjacent the proximal end of the shaft for manipulating the electrode from outside the patient body.

In yet another aspect, the present invention provides a probe for heating and contracting target tissues. The probe comprises a shaft having a proximal end and a distal end. At least one electrode is disposed near the distal end of the shaft. A handle is disposed adjacent the proximal end of the shaft for manipulating the at least one electrode from outside the patient body. The handle supports a battery and circuitry for energizing the at least one electrode with sufficient RF electrical potential to heat and contract the target tissue.

Circuitry for converting a direct current to an alternating current will often be coupled to the battery to provide heating while avoiding nerve and/or muscle stimulation. In many embodiments, a control system will be coupled to the electrode so that the target tissue is raised to a temperature within a predetermined range. The temperature of the target tissue may be determined by a tissue temperature sensor disposed near the electrode (ideally being disposed between bipolar electrodes) and/or by monitoring the impedance, resistance, or other electrical characteristics of the tissue/electrode circuit.

In another embodiment, the present invention provides a probe for shrinking collagenated tissue of a patient body. The probe comprises a shaft having a proximal end and a distal end. A grasper is disposed near the distal end of the shaft, and is adapted to draw a region of the tissue inward so as to reduce tension within the region. An energy applying member is disposed adjacent to the grasper. The energy applying member is capable of heating the tissue while the tension is reduced so that the tissue contracts, but without substantially ablating the tissue.

The present invention also provides a method to treat a hyperextending support tissue of a patient body. The hyperextending tissue has a tissue depth, and the method comprises electrically coupling the first electrode to the hyperextending tissue. A second electrode is also electrically coupled to the hyperextending tissue, and an electrical potential is applied across the electrodes while controlling a separation between the first and second electrodes. As a result of this separation control, an electrical current within the hyperextending tissue heats and shrinks the hyperextending tissue, but heating of tissue beyond the tissue depth is minimized.

The present invention also provides a method to treat urinary stress incontinence. The method comprises introducing a probe into a patient body and aligning the probe with a pelvic support tissue within the patient body. The probe is energized to heat and contract a portion of the pelvic support tissue.

In most embodiments, a portion of the pelvic support tissue is gently and resistively heated to between about 60° C. and 110° C., often being between about 60° C. and 80° C., by applying an electrical potential across the electrodes, the electrodes being adapted to engage the fascia surface. This gentle bipolar resistive heating will often be targeted at fascia. Such contraction of the fascia can raise and/or reposition the bladder within the patient body when the fascia is heated to a depth of less than about 2.8 mm, preferably to a depth of less than about 2.0 mm, thereby minimizing collateral injury to the surrounding tissues. The heating depth can be precisely limited by controlling the diameter of the electrode surfaces (electrode surface diameter typically in the range from about 0.25 mm to about 4.0 mm, often being from about 0.25 mm to about 2.0 mm) and the ratio of the spacing between the electrodes to the electrode surface diameter (the spacing typically being between about 1.0 and 4.0 times the surface diameter). Advantageously, a preferred separation distance of between about 2 and 3 times the electrode surface diameters will provide an effective heating depth of about 2 times the electrode surface diameter. Surprisingly, sufficient RF energy for such targeted heating can be provided by a battery pack within a handle of the probe, the battery typically providing between about 5 and 20 watts.

In a second aspect, the present invention provides an endoscopic method for treating urinary stress incontinence. The method comprises introducing a probe into a patient body, and optically imaging the probe and a target tissue. The target tissue comprises a portion of an endopelvic fascia or an arcus tendineus fascia pelvis. The electrode is positioned against the target tissue, and energized to heat and contract the target tissue, without substantially ablating the target tissue.

Once again, heating will often be limited in depth through the use of a bipolar probe having a predetermined electrode diameter, spacing between the electrodes, and power. Heating can be monitored and/or controlled, optionally using feedback from a temperature sensor mounted between the electrodes. Advantageously, repeatedly sweeping the electrodes across the endopelvic fascia can raise the bladder by discrete increments, typically by between about 0.1 and 3.0 mm with each sweep of the electrodes.

In another aspect, the present invention provides a least invasive method for controllably shrinking fascia. The method comprises inserting a probe into a patient body while the probe is in a narrow configuration. The probe has first and second electrodes, and is expanded to a wider configuration to deploy at least one of the first and second electrodes. The deployed electrodes are engaged against the fascia, and an electrical potential is applied across the electrodes to heat and contract the fascia disposed therebetween.

In yet another aspect, the present invention provides a method for treating a hernia. The hernia comprises a structure which protrudes through a containing tissue. The method comprises applying sufficient energy to the containing tissue adjacent the hernia to heat the containing tissue so that the containing tissue contracts. The contraction mitigates the hernia, but the heat does not substantially ablate the containing tissue.

In another aspect, the invention provides an abdominoplasty method for tightening an abdominal wall. The abdominal wall comprises a fascia, and the method comprises applying sufficient energy to the abdominal wall to heat the fascia so that the abdominal wall contracts. The heat is applied without substantially ablating the abdominal wall and adjacent tissues.

In yet another aspect, the invention provides a method to treat a hyperextending collagenated support tissue of a patient body. The method comprises grasping a region of the hyperextending tissue and drawing the hyperextending tissue inward so as to decrease tension in the region. At least a portion of the drawn region is heated so that the region shrinks, wherein the region is heated without substantially ablating the hyperextending tissue.

In yet another aspect, the invention provides a kit for shrinking a target collagenated tissue within a patient body. The target tissue has a tissue depth, and the kit comprises a probe and instructions for operating the probe. The probe includes a shaft having a proximal end and a distal end. First and second electrodes are disposed near the distal end of the shaft, the electrodes defining a separation distance therebetween. The instructions include the steps of electrically coupling the first and second electrodes with the target tissue, and heating and contracting the target tissue without ablating the target tissue by directing an electrical current flux through the target tissue between the electrodes. The separation distance substantially limits heating beyond the target tissue depth.

In yet another aspect, the invention provides a kit for treating urinary stress incontinence of a patient with a lax pelvic support structure. The kit comprises a probe having a heating element and instructions for operating the probe. Instructions include the steps of coupling the heating element to the pelvic support structure, and applying an amount of energy with the heating element to the pelvic support structure. The energy is sufficient to cause shrinkage of the pelvic support structure, and the shrinkage inhibits urinary incontinence.

In yet another aspect, the invention provides a kit for treating a hernia. The hernia comprises a structure which protrudes through a collagenated containing tissue. The kit comprises a probe having a heating element and instructions for operating the probe. The instructions include the steps of coupling the probe to the containing tissue, and applying an amount of energy from the probe to the containing tissue. The energy is sufficient to heat the containing tissue so that the containing tissue shrinks to mitigate the hernia.

In one exemplary embodiment of the present method, energy is applied from within the patient's urethra, typically by inserting an energy-applying probe into the urethra without having to employ any percutaneous or transmucosal penetrations or incisions. When using such a urethral probe, the energy will typically be applied directly to the urethral wall, either to a single location aligned with the urethral sling or to at least two sites including a first site upstream of the urethral sling and a second site downstream of the urethral sling. By "urethral sling," we mean those supporting tendons and other tissue structures which extend from the pubic bone downward beneath the urethra and urethral sphincter. Application of energy at such location(s) acts to shrink tissue adjacent the urethral lumen and to provide selective "kinks" or closure points at which the urethra can be closed.

In an alternative exemplary embodiment, energy-applying elements are penetrated directly into the pubococcygeal muscles, the iliococcygeal muscles, and/or detrusor urinae muscles (and adjacent fascia) which support the urethra and urinary sphincter. By applying energy directly into these supporting muscles and tissue structures, the muscles can be contracted to provide improved urinary continence. In particular, sufficient muscular integrity can be provided so that urinary leakage does not result from transient increases in intra-abdominal pressure as a result of stress. In the illustrated embodiment, the electrodes are penetrated into the target muscles through the vagina, typically using an introducer having an array of extensible electrodes arranged to contact the target muscles and/or tendons.

In these exemplary embodiments, the energy will typically be applied using an electrode capable of delivering radio frequency (RF) energy directly against the urethral wall or into the supporting tissues in a monopolar or bipolar manner. In the first embodiment, electrodes will usually be surface electrodes, i.e., adapted to contact the luminal wall of the urethra without penetration. In the second embodiment, the electrodes are fashioned as needles or other penetrating members which can penetrate into the urethral wall by a desired distance. In addition to electrodes, the heat-applying elements can be optical fibers (for delivery laser or other light energy), resistive heating elements, inductive heating elements, microwave heating elements, or any other device which can be externally powered to heat tissue to the temperatures and for the times discussed below.

The methods of the present invention may also be performed using devices and systems which access the treated tissue structures from sites other than the urethra or vagina. For example, energy-applying probes can be introduced percutaneously from the patient's abdomen to a desired treatment site, for example the pubococcygeal muscle and tendon, or may alternatively be introduced through the rectum. Alternatively, in female patients, the energy-applying probes can be transmucosally introduced through the vagina, as discussed above. For the purposes of the present invention, it is necessary only that the energy be delivered to a target tissue structure in a manner which permits heating of the tissue to a desired temperature and for time sufficient to contract the tissue by a desired amount.

In addition to RF energy, the devices, systems, and methods of the present invention can rely on other energy sources, such as microwave, light (laser) energy, electrical resistance heating, the delivery of heated fluids, the focusing of ultrasound energy, or any other known energy delivery technique which can be targeted to specific tissue and raise the tissue temperature to the desired range.

When energy is applied directly to the luminal wall, it will be desirable to control the resulting cross-sectional area of the urethra. Usually, the cross-sectional area will be reduced. Control of the amount of reduction can be effected, for example, by placing the energy-applying elements, such as RF electrodes, on an expandable member which can initially be expanded to contact the elements against the luminal wall. As the luminal wall shrinks, the cross-section area of the expandable member can also be reduced. Alternatively, in instances where the energy is being applied to contract adjacent tissue structures, it may be necessary to further expand the expandable member carrying the electrodes to maintain contact. A variety of specific configurations can be utilized.

In some embodiments, devices according to the present invention will comprise a probe body having a proximal end and a distal end. The body will preferably have a length and diameter selected to permit introduction into the urethra or vagina so that the distal end can be positioned adjacent to the urethral sling or target tissues. One or more electrodes are disposed on the distal end of the probe body to apply energy into the urethral wall in the region of the urethral sling and/or into the tissue structures which support the urethral sling. A connector is provided on the proximal end of the probe body to permit connection to an appropriate power supply. The probe body will typically have a length in the range from 5 cm to 20 cm with electrode lengths in the range from 0.3 cm to 7 cm. The probe body will usually have a diameter in the range from 1 mm to 6 mm. The body will usually be flexible, but could also be rigid. The body should have sufficient torsional rigidity to permit rotational orientation and alignment of the probe within the urethra. The probe will include at least a single electrode, and will often include two or more electrodes which can be connected to the power supply in a monopolar or a bipolar fashion. The electrodes may be surface electrodes (for engaging the urethra wall) or tissue-penetrating electrodes for applying energy into the urethra-supporting tissues. In a specific embodiment, the probe will include two axially-spaced apart electrodes which are positioned and configured so that they will be aligned on the upstream and downstream sides of the urethral sling when applying energy within the urethra. The probe may further comprise an expansion member, such as an expandable balloon, carrying at least one of the electrodes on the catheter body. In a second specific embodiment, the probe includes an array of extensible, tissue-penetration electrodes disposed to penetrate target tissues from the vagina.

DESCRIPTION OF THE SPECIFIC EMBODIMENTS

The present invention generally provides devices, methods, and systems which can selectively shrink fascia and other collagenated tissues. By directing an electrical current flux through such a tissue, ideally between bipolar electrodes directly engaging the tissue, the electrical resistance of the tissue can induce gentle heating and contraction of the tissue without significant injury to the adjacent tissues. Controlling a diameter of the electrode surfaces and a ratio of the surface diameter to a separation distance between the electrodes can limit the depth of heating, while electrode surface shape and size will help determine heating at the electrode/tissue interface. The present invention is particularly well adapted for contraction of fascia and ligaments, and may therefore have applications in a variety of therapies, including traditional and minimally invasive therapies of the pelvis, thorax, and joints. These devices, methods, and systems are adaptable for therapies of specific tissues and conditions including hiatal hernias, abdominal hernias, cystocele, enterocele, rectocele, and uterovaginal prolapse. The present invention will find its most immediate application for the treatment of urinary stress incontinence. In many embodiments, the present invention will effect contraction of a pelvic support tissue to raise a position of the bladder, particularly after the pelvic support tissues have been stressed by pregnancy. Related devices and methods are described in co-pending U.S. patent application Ser. No. 08/910,775 filed on Aug. 13, 1999, the full disclosure of which is incorporated herein by reference.

In general, the present invention is well adapted for treatment of any hyperextending collagenated tissue. As used herein, the term "hyperextending" encompasses any tissue structure which is excessive in at least one dimension, so that a support function of the tissue is compromised. This excessive length, etc., may be the result of injury, pregnancy, disease, age, a congenital defect, a tear or partial tear, or the like.

Figure 1:
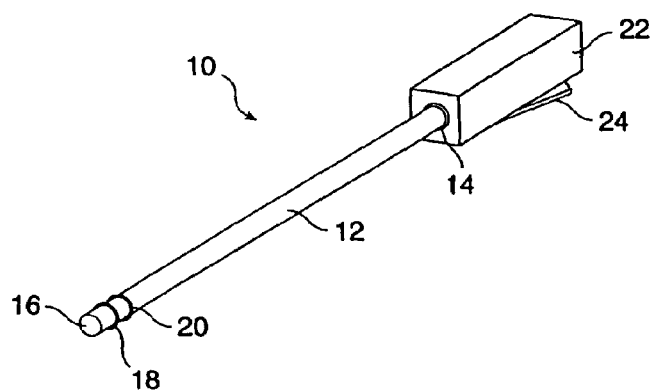
FIG. 1 is a perspective view of a bipolar battery operated probe for laparoscopically heating and contracting fascia, according to the principles of the present invention.

Referring now to FIG. 1, a tissue contraction probe 10 includes a shaft 12 having a proximal end 14 and a distal end 16. First and second electrodes 18, 20 are disposed near distal end 16 of shaft 12, while a handle 22 is disposed at the proximal end of the shaft. A switch 24 applies a radiofrequency electrical potential across first and second electrodes 18, 20 to effect gentle resistive heating of electrically conductive tissues which span these electrodes. Surprisingly, power requirements of this targeted bipolar resistive heating are so low that a battery pack contained within handle 22 can sufficiently energize first and second electrodes 18, 20.

Figure 2:
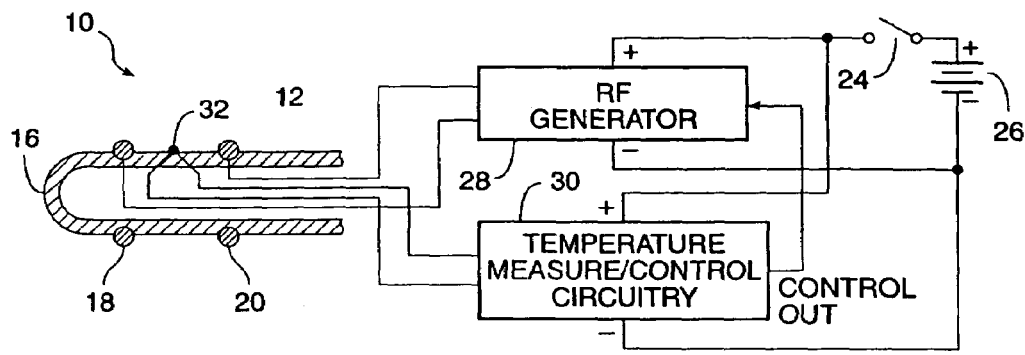
FIG. 2 is a schematic of the functional components of the probe of FIG. 1.

As can be understood with reference to FIG. 2, a battery pack 26 energizes probe 10, typically providing a relatively low power radio frequency current. The direct current of the battery is converted to the desired radio frequency by a DC to AC converter of a RF generator 28. The electrical potential applied to first and second electrodes 18, 20 will typically be between about 200 and 1,000 KHz, and will typically have an amplitude of between about 10 and 100 volts ac rms. Such low power heating will substantially avoid arcing between the electrode and the tissue surface, further decreasing the injury to these tissues, and also providing safety to the operator. The RF electrical heating will also desiccate the tissue, increasing its resistance. Since the applied voltage is too low to cause arcing, the delivered power will decrease as the tissue dries, so the tissue damage is superficial and self limiting. This makes treatment less subject to operator error.

A heating controller 30 will often limit at least one of the following: the temperature of the target tissue, the shrinkage of the tissue between the electrodes, and/or the time the target tissue is maintained at an elevated temperature. In some embodiments, tissue heating temperatures will be measured directly using a temperature sensor 32 mounted to the probe between the first and second electrodes 18, 20, or separately inserted into the tissue via an ultrasonically or fluoroscopically guided temperature probe. Alternatively, tissue temperature, contraction, and the like may be determined indirectly by monitoring the electrical characteristics of the tissue itself. In other words, by monitoring the circuit during heating, the tissue resistivity, resistance, capacitance, or the like, can be calculated. From these values, and optionally by monitoring the changes in these electrical characteristics, it may be possible to estimate the temperature or degree of desiccation of the tissue, the amount of shrinkage which has occurred, and the like. Preferably, controller 30 will limit the heating of tissues to a temperature range of between about 60° C. and 110° C., ideally to between about 60° C. and 80° C.

Alternatively, it may be possible to simply limit the electrical potential applied across the electrodes thereby permitting normal thermal conduction to control the maximum temperature. In fact, in some embodiments, a simple timer may be coupled to switch 24, so that a limited amount of energy is applied across first and second electrodes 18, 20, thereby avoiding over-treatment (particularly during spot treatments, as described hereinbelow). The physician simply energizes the time limited circuit after each movement of the electrodes, thereby avoiding unintended over-treatment, and also helping to ensure that sufficient energy is delivered for treatment of each site.

While the exemplary embodiment incorporates battery pack 26 and controller 30 into handle 22, it should be understood that the energizing and control functions may be provided by structures which are external to probe 10. In such embodiments, couplers for connecting electrodes 18 and 20 to a power source, control circuitry, and the like, will often be provided on housing 22. Battery pack 26 may optionally include two or more batteries. As used herein, a battery may be a single cell or a series of cells, where each cell is a substantially self-contained D.C. energy source.

Figure 3:
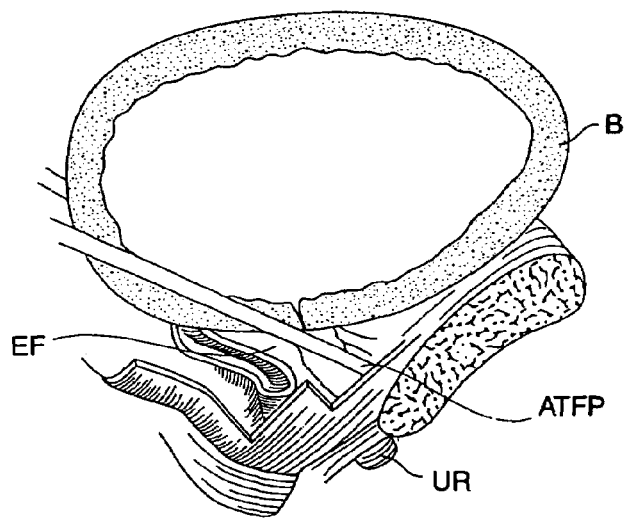
FIG. 3 is a lateral cross-sectional view showing the urinary bladder and bladder support structures.

The pelvic support tissues which generally maintain the position of the urinary bladder B are illustrated in FIG. 3. Of particular importance for the method of the present invention, endopelvic fascia EF defines a hammock-like structure which extends between the arcus tendineus fascia pelvis ATFP, as can be understood with reference to FIG. 4, these latter structures extend substantially between the anterior and posterior portions of the pelvis, so that the endopelvic fascia EF largely defines the pelvic floor.

In women with urinary stress incontinence due to bladder neck hypermobility, the bladder has typically dropped between about 1.0 and 1.5 cm (or more) below its nominal position. This condition is typically due to weakening of the pelvic support structures, including the endopelvic fascia, the arcus tendineus fascia pelvis, and the surrounding ligaments and muscles, often as the result of bearing children.

When a woman with urinary stress incontinence sneezes, coughs, laughs, or exercises, the abdominal pressure often increases momentarily. Such pressure pulses force the bladder to descend still further, shortening the urethra UR and momentarily opening the urinary sphincter.

As can be most clearly understood with reference to FIGS. 3–7, the present invention generally provides a therapy which applies gentle heating to shrink the length of the support tissues and return bladder B to its nominal position. Advantageously, the bladder is still supported by the fascia, muscles, ligaments, and tendons of the original pelvic support tissues. Using gentle resistive heating between bipolar electrodes, the endopelvic fascia EF and arcus tendineus fascia pelvis ATFP are controllably contracted to shrink them and re-elevate the bladder towards its original position.

Tissue contraction with probe 10 will generally be performed in at least one of two modes: spot treatments and line treatments. For example, by engaging the arcus tendineus fascia pelvis at a substantially fixed location with first and second electrodes 18, 20, a discrete portion along that substantially linear structure can be gently heated for a few seconds to the target temperature range. The tough fibrous tendon will then shorten, raising the endopelvic fascia EF which, in turn, raises the overall position of bladder B. Such contractions of a discrete region about a fixed engagement location are herein called spot treatments.

Figure 4:
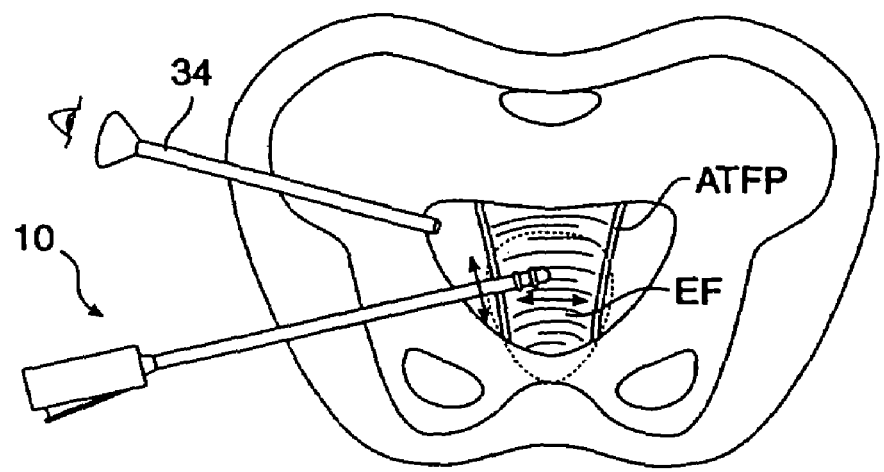
FIG. 4 is a simplified cross-sectional view of the pelvis showing the endopelvic fascia and arcus tendineus fascia pelvis, and illustrates a method for treating urinary stress incontinence by sweeping the probe of FIG. 1 across the endopelvic fascia to reposition and/or raise the urinary bladder.

To provide a line treatment, the distal end of probe 10 is swept across endopelvic fascia EF laterally or linearly, as illustrated in FIG. 4. As the electrodes engage the adjacent endopelvic fascia, they raise the temperature of the adjacent tissues, resulting in a line of contracted tissues behind and between the electrode paths. Advantageously, this line of fascia contraction increases the overall tautness of the endopelvic fascia, again raising the overall position of bladder B. This is an example of the use of a single line treatment to effect repositioning of the bladder.

Advantageously, repeatedly sweeping probe 10 across adjacent areas of the endopelvic fascia can raise the bladder in discrete increments. For example, if first and second electrodes 18, 20 are separated by a space of about 3.0 mm, and if the fascia shrinks by about 50% with it each sweep of probe 10, the physician can re-elevate bladder B about 1.5 cm with between 10 and 15 line treatments of the endopelvic fascia. Similar results may be provided by 10 to 15 spot treatments of the arcus tendineus fascia pelvis, or by some combination of spot and line treatments.

Access to and direction of the therapy, as schematically illustrated in FIG. 4, will often be provided by the minimally invasive methods and devices that have recently been developed. In many embodiments, a laparoscope 34 will allow direct optical imaging, often while the pelvic region is distended using gas insufflation. The present methods may be optically directed using a variety of existing endoscopic structures, depending on the treatment site and access approach. Laparoscopes, arthroscopes, hysteroscopes, or the like may be used (or adapted for use) in the present methods. Alternatively, conventional optical imaging capabilities may be incorporated into probe 10, or specialized fiber optic image guides may be used, either separated from or incorporated into probe 10. In some embodiments, the therapy may be directed using a remote imaging modality, such as fluoroscopy, ultrasound, magnetic resonance imaging, or the like. It is also possible to take advantage of the controlled tissue contraction of the present invention in a more traditionally invasive therapy.

Figure 5:
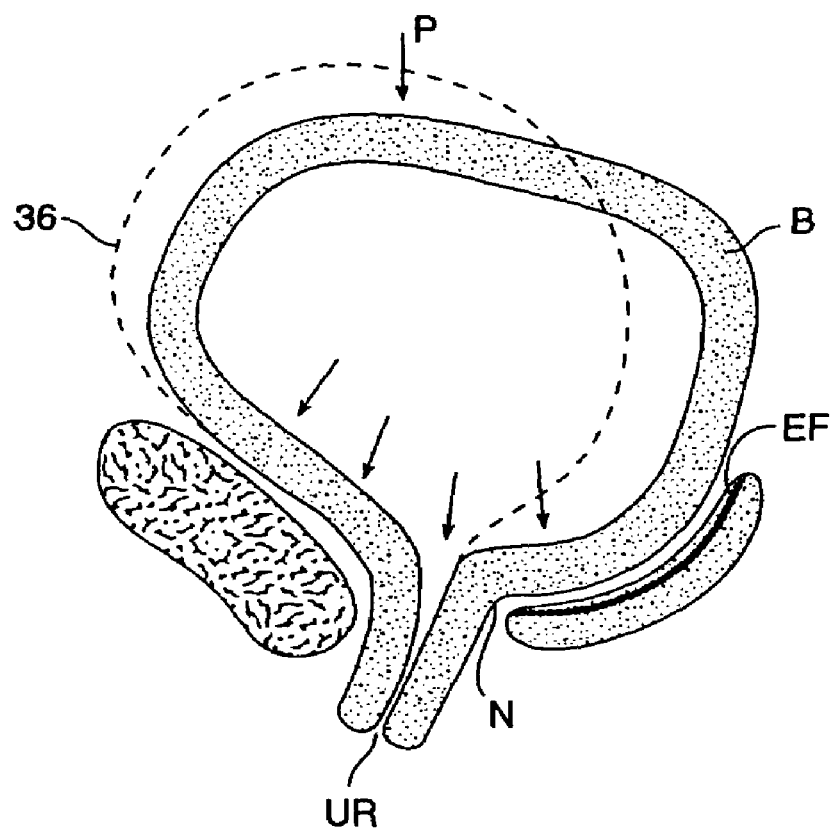
FIG. 5 is a cross-sectional view of a patient suffering from urinary stress incontinence due to inelastic stretching of the endopelvic fascia.

Referring now to FIG. 5, bladder B can be seen to have dropped from its nominal position (shown in phantom by outline 36). While endopelvic fascia EF still supports bladder B to maintain continence when the patient is at rest, a momentary pulse P opens the bladder neck N resulting in a release through urethra UR.

Figure 6:
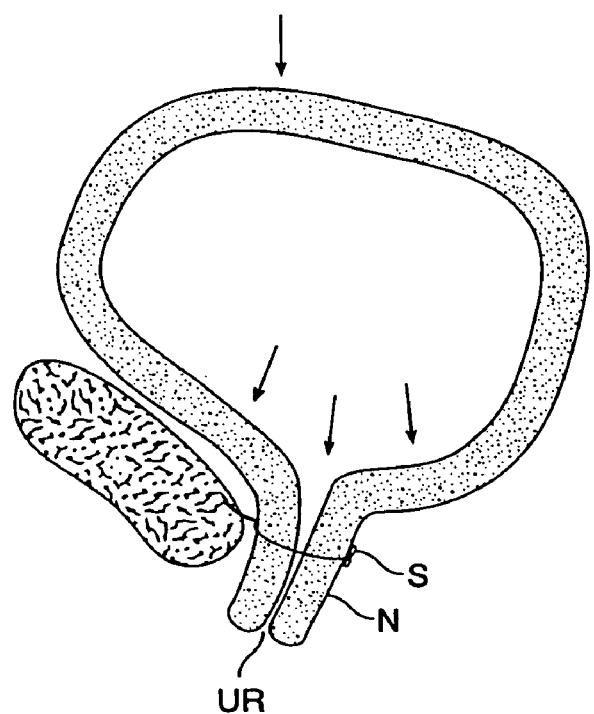
FIG. 6 shows a known method for treating urinary stress incontinence by affixing sutures around the bladder neck.

A known treatment for urinary stress incontinence relies on sutures S to hold bladder neck N closed so as to prevent inadvertent voiding, as seen in FIG. 6. Sutures S may be attached to bone anchors affixed to the pubic bone, ligaments higher in the pelvic region, or the like. In any case, loose sutures provide insufficient support of bladder neck N and fail to overcome urinary stress incontinence, while overtightening of sutures S may make normal urination difficult and/or impossible.

Figure 7:
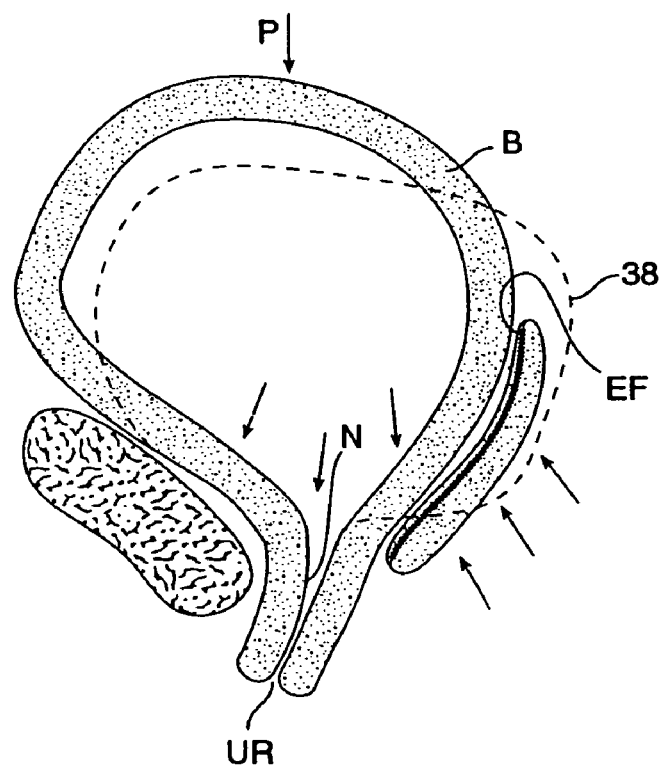
FIG. 7 illustrates improved bladder support provided by selectively contracting the endopelvic fascia as a therapy for urinary stress incontinence, according to the principles of the present invention.

As shown in FIG. 7, by selectively contracting the natural pelvic support tissues, bladder B can be elevated from its lowered position (shown by lowered outline 38). A pressure pulse P is resisted in part by endopelvic fascia EF, which supports the lower portion of the bladder and helps maintain the bladder neck in a closed configuration. In fact, finetuning of the support provided by the endopelvic fascia is possible through selective contraction of the anterior portion of the endopelvic fascia to close the bladder neck and raise bladder B upward. Alternatively, lateral repositioning of bladder B to a more forward position may be effected by selectively contracting the dorsal portion of endopelvic fascia EF. Hence, the therapy of the present invention may be tailored to the particular weakening exhibited by a patient's pelvic support structures.

Figure 7A:
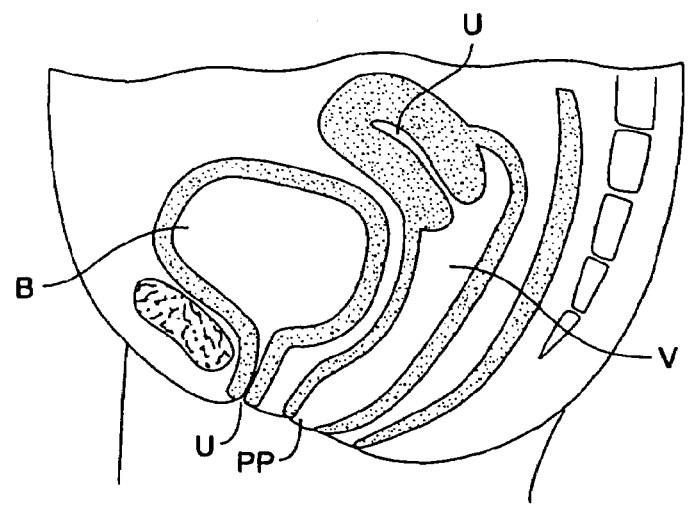
FIG. 7A illustrates a patient suffering from a cystocele in which the bladder protrudes into the vagina, and which may be treated by selectively contracting the pelvic support tissues using the methods of the present invention.

Another condition which is suitable for treatment using the methods of the present invention is illustrated in FIG. 7A. In this patient, a posterior portion PP of bladder B protrudes into vagina V so that an acute angle is formed by the posterior wall of the urethra and the anterior wall of the urinary bladder. Such a condition, generally referred to as cystocele, may be effectively treated by selectively contracting the endopelvic fascia and/or other pelvic support tissues and repositioning the bladder as described above. Additional conditions which may be treated using the methods of the present invention include enterocele (a hernial protrusion through a defect in the rectovaginal or vesicovaginal pouch), rectocele (prolapse or herniation of the rectum), and uterovaginal prolapse (downward movement of the uterus so that the cervix extends into or beyond the vaginal orifice, usually from injuries during childbirth or advanced age). For each of these conditions, the methods of the present invention generally make use of the natural support tissues within the pelvis, generally by selectively contracting those support tissues to reposition and/or contain the displaced organs. As will be described in more detail hereinbelow, herniated structures may be treated at least in part by repositioning the protruding structures behind the tissue which nominally contain them, and then selectively contracting the containing tissues to prevent reoccurrence of the hernia.

Figure 8:
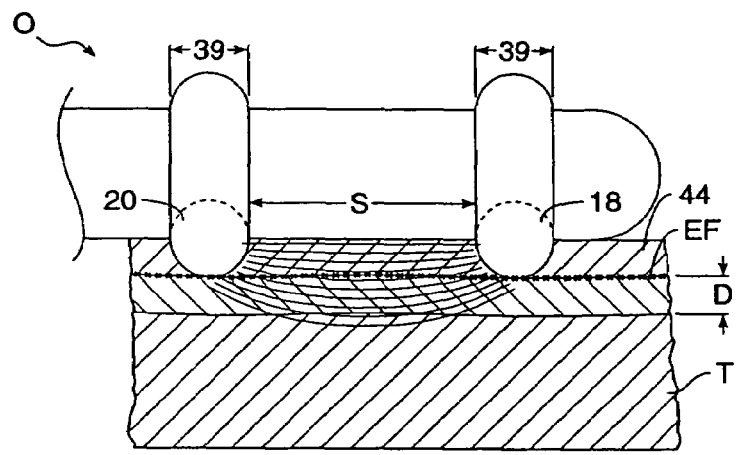
FIG. 8 illustrates how the controlled spacing between the bipolar electrodes of the probe of FIG. 1, relative to the electrode diameter, limits the depth of tissue heating.
Figure 9:
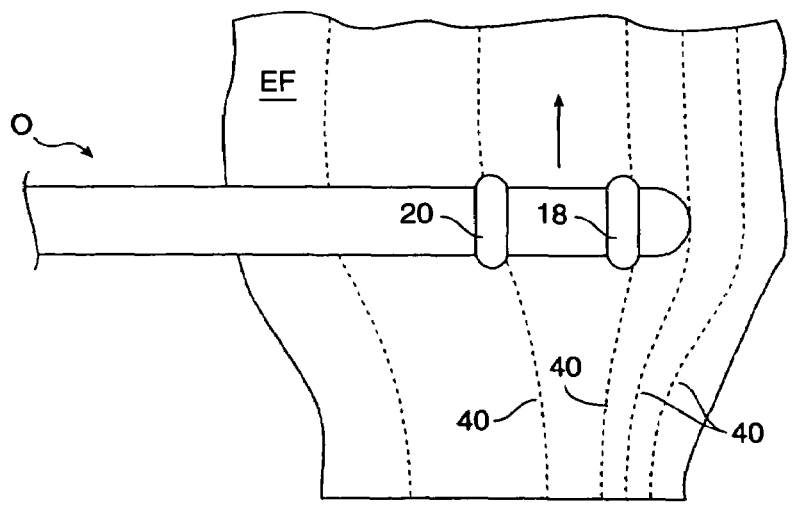
FIG. 9 schematically illustrates repeatedly sweeping the bipolar electrodes of the probe of FIG. 1 across the endopelvic fascia to raise the urinary bladder in a series of discrete increments.

Referring now to FIGS. 8 and 9, a depth D of the endopelvic fascia EF (and adjacent tissue T) heated by bipolar probe 10 will depend on the power applied, on a spacing S between first and second electrodes 18, 20, and on the surface diameter 39 of the electrodes. Generally, spacing S will be between about 0.25 and 4.0 mm. More specifically, spacing S will preferably be in the range from about 1 to 4 times the electrode diameter 39, with the electrode diameter often being between about 0.25 and 4.0 mm, preferably being between about 0.25 and 2.0 mm, and ideally being between 0.25 and 1.0 mm. This will limit the heating depth D to generally less than about 2.0 mm, and often to less than 1.0 mm. Advantageously, the temperature gradient along the edge of the treatment zone is quite steep. By such selective heating of the endopelvic fascia EF, collateral damage to the underlying tissues T is limited. Fascia will contract when heat is applied by such a structure for a very short time, the target tissue ideally being heated for a time in a range from about 0.5 to 5 seconds. In general, selectively targeting the fascia adjacent the surface maximizes the tissue contraction provided by heating, and greatly limits necrosis, lesioning, and other collateral injuries to the vaginal mucosa and the muscular tissues which help to support the bladder in the desired position. As more fully explained in application Ser. No. 08/910,775 filed Aug. 13, 1997, the electrodes may be cooled to prevent injury to the engaged tissue surface. Cooling may be provided, for example, by forming the electrodes of thermally conductive tubing, and by running a cold fluid through the tubing.

As illustrated in FIG. 8, a film 41 of saline, either natural or introduced, may be disposed over the engaged tissue surface. Film 41 prevents the electrode surfaces from sticking to the engaged tissue, and can also provide a more even impedance and/or power through the circuitry. Drying of the tissue surface due to $CO_2$ insufflation may be avoided by providing a saline irrigation of about 1 cc/min. during the tissue contraction procedure.

While spacing S will often be fixed, it should also be understood that the separation between the first and second electrodes may optionally be varied to controllably vary the heating depth D.

The sweeping of first and second electrodes 18, 20 of probe 10 over the endopelvic fascia EF to discretely raise the bladder can be understood with reference to FIG. 9. The endopelvic fascia EF is heated and contracted by the passing electrodes, the fascia typically contracting by an amount within the range between about 30 and 50%. As the electrodes sweep across the fascia surface, they define electrode paths 40. The electrode paths are closer together after probe 10 has swept by, so that the overall width of the endopelvic fascia decreases by an amount of between about 0.3 and 0.5 times electrode spacing S each time probe 10 sweeps over untreated fascia (in our example). Hence, the total distance that the bladder is raised can be varied by varying the number of sweeps of probe 10. The probe will preferably sweep a different section of the endopelvic fascia each time, as fascia which has previously been contracted will undergo only a more limited contraction. Hence, probe 10 will often be moved axially by an amount of at least the electrode spacing S prior to each sweep.

Figure 10:
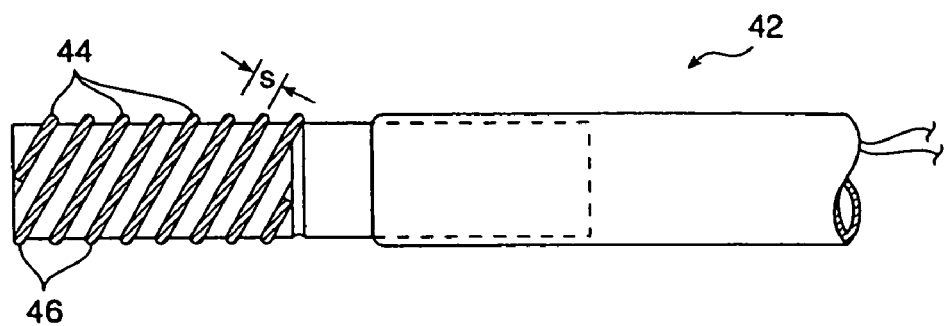
FIGS. 10–12D illustrate alternative electrode configurations for use with the probe of FIG. 1.
Figure 11A:
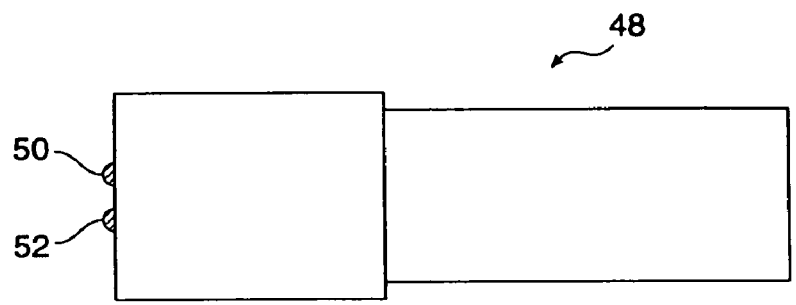
Figure 11B:
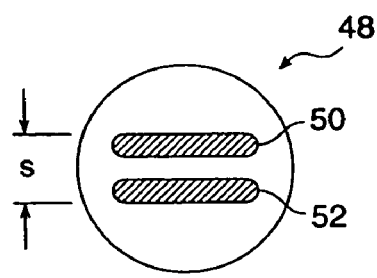
Figure 12A:
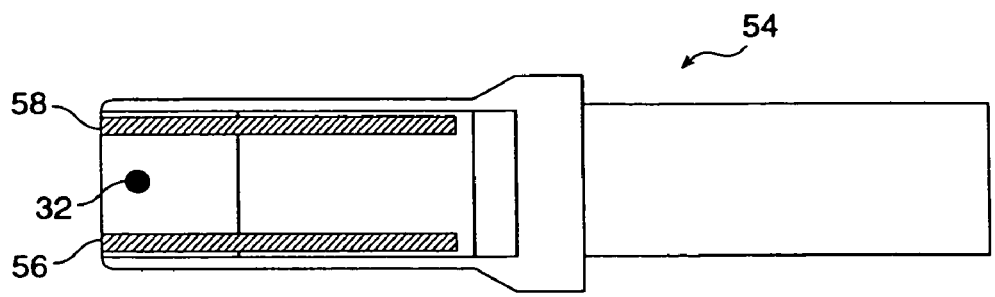
Figure 12B:
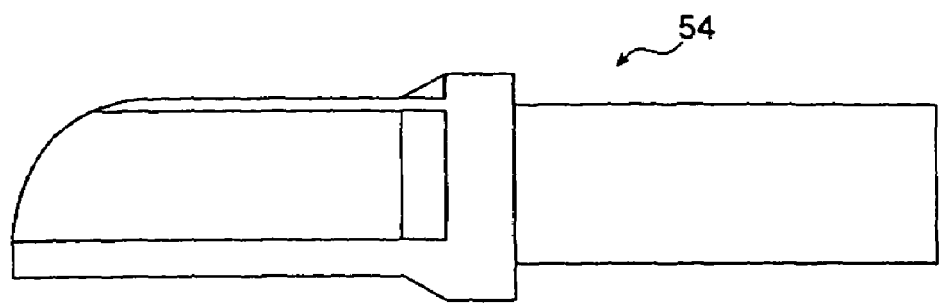
Figure 12C:
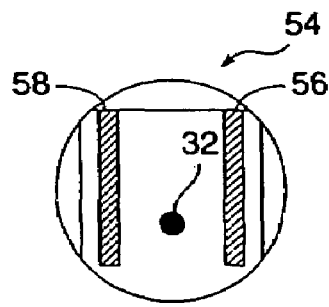
Figure 12D:
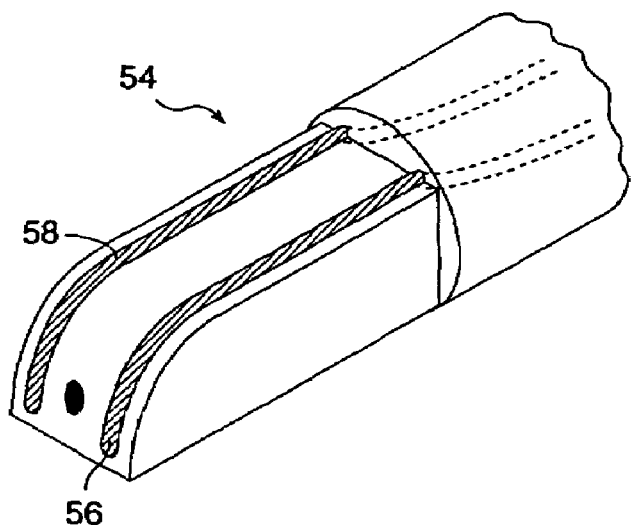

A variety of alternative electrode configurations are illustrated in FIGS. 10–12D. FIG. 10 illustrates a probe 42 which is otherwise similar to probe 10 of FIG. 1, but which includes first and second interleaved helical electrodes 44, 46. These electrodes alternate about the distal end of helical probe 42 in a "barber pole" configuration. This allows a greater amount of shrinkage each time helical probe 42 engages a fascia or ligament surface, as heating will be provided between each span of the tissue between adjacent electrodes, and also eliminates any need for angular alignment of the probe. Advantageously, spacing S remains substantially uniform over the probe surface.

Distally oriented probe tip 48 includes first and second distally oriented electrodes 50, 52 which are again separated by spacing S. This structure is particularly well-suited for contracting tissues having surfaces which are oriented normal to the axis of the probe, and for spot contraction of certain tissue bands (such as ligaments). An axially-ended probe tip 54 includes alternating first and second axially-ended ribbon or wire electrodes 56, 58, and is adapted for engaging both laterally and proximally oriented tissue surfaces. Note that axial first and second electrodes 56, 58 may comprise ribbon structures or wires which are inset into axially-ended electrode tip 54, thereby avoiding inadvertent engagement of tissues adjacent the target tissue surface. Sensor 32 optionally measures the temperature of the target tissue.

Figure 13A:
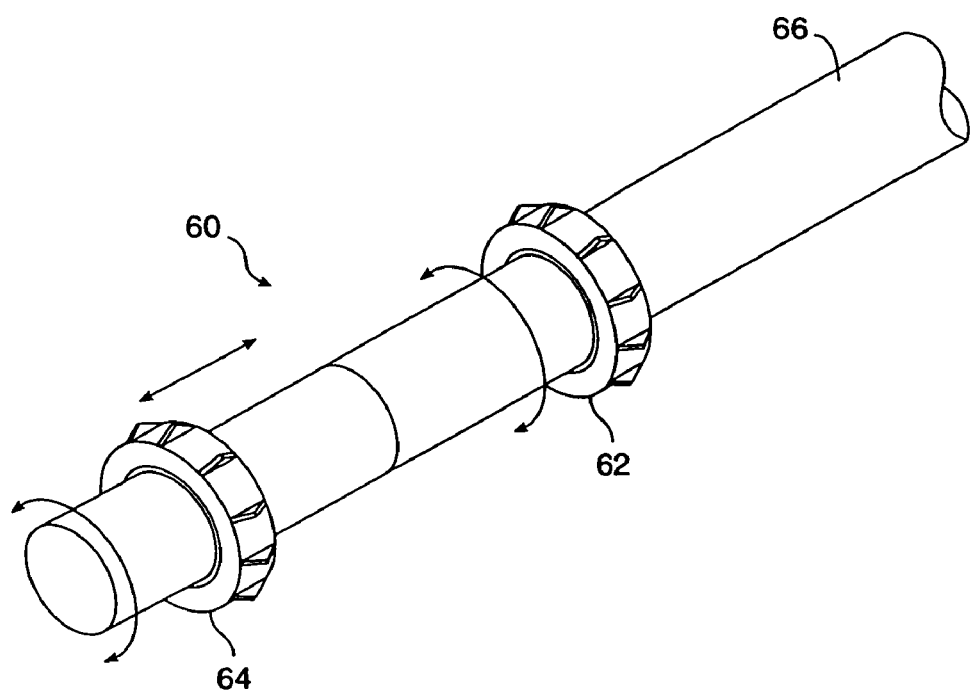
FIGS. 13A and 13B illustrate bipolar electrodes which move relative to each other when tissue contracts to provide feedback and/or limit tissue heating, according the principle of the present invention.

In some embodiments, the electrode structures on the probes of the present invention will provide feedback to the probe regarding the amount of tissue contraction. Referring now to FIG. 13A, a moveable electrode probe 60 includes rotatable first and second electrodes 62, 64 which roll about a shaft 66 to facilitate sweeping of the electrodes over the target surface. The electrodes also include radial protrusions, presenting a structure which looks somewhat like a gear with pointed teeth. The protrusions minimize sliding between the electrode surface and the target tissue surface. Hence, as the engaged tissue contracts along the axis of shaft 66, it draws the first and second rotatable electrodes 62, 64 together.

By measuring the displacement between first electrode 62 and second electrode 64, moveable electrode probe 60 provides an indication of the total tissue shrinkage. The attending physician or an electronic electrode energizing control circuit may make use of this feedback to control tissue heating. Alternatively, the probe may measure the force the contracting tissue imposes on the electrodes without allowing any actual displacement of one electrode relative to the other. Such a structure would maintain the fixed spacing S between the electrodes.

Figure 13B:
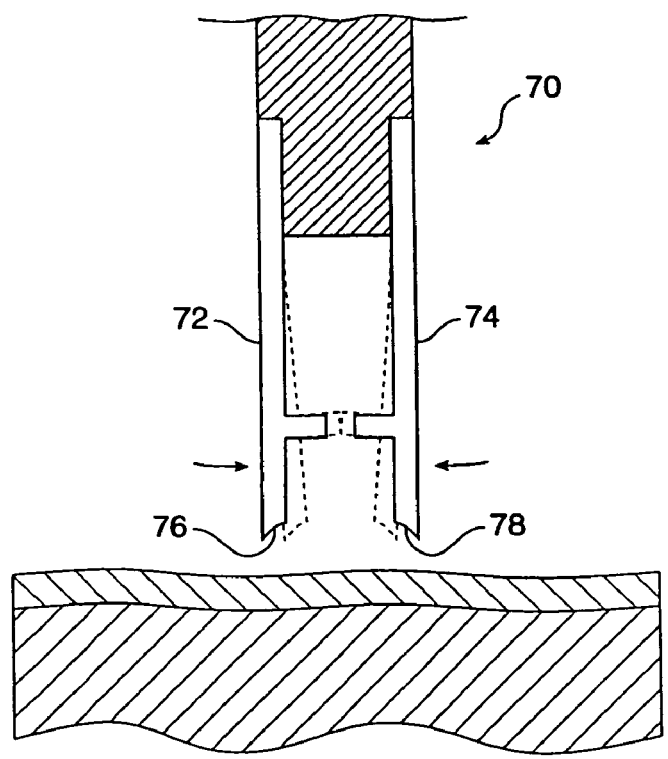

An even simpler feedback mechanism is illustrated in FIG. 13B. Spot contraction probe 70 includes first and second shortable electrodes 72, 74 which will contact each other when the engaged tissue is contracted by a predetermined amount. The shorting of the electrodes will often provide a signal terminating the energizing of the electrodes. The electrodes will optionally have protrusions 76 which press into the tissue surface to avoid sliding.

Those with skill in the art will realize a variety of mechanisms may be used to measure shrinkage of the tissue, including fiber optic measuring mechanisms, microswitches, strain gauges, or the like. However, the electrode structure illustrated in FIG. 13B has the advantage that the shorting of the electrodes automatically terminates heating, allowing the device to both measure and control shrinkage with a very simple structure.

Figure 13C:
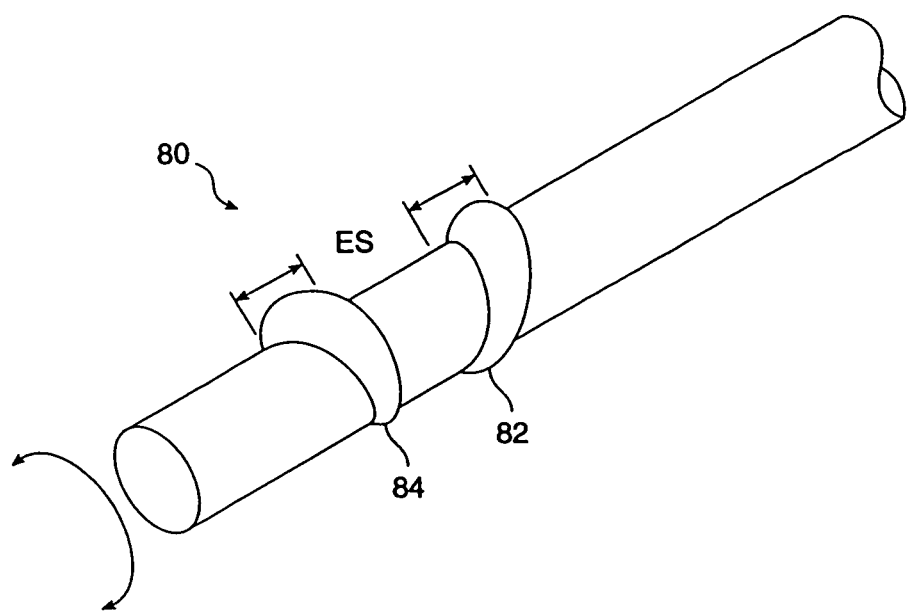
FIG. 13C illustrates an electrode structure that varies the heating depth with the rotational position of the probe about the axis of the probe.

In some embodiments, a variable spacing between first and second bipolar electrodes may allow the surgeon to control the depth of heating. For example, as illustrated in FIG. 13C, rotating a variable spacing probe 80 allows the physician to engage a target tissue surface with alternate portions of angled electrodes 82, 84 to vary an effective spacing ES therebetween. Note that local electrode surface diameters of angled electrodes 82, 84 vary with separation, so that a ratio of electrode separation ES to local surface diameter remains about 2 to 1. Clearly, more complex spacing varying mechanisms are also possible.

Figure 14:
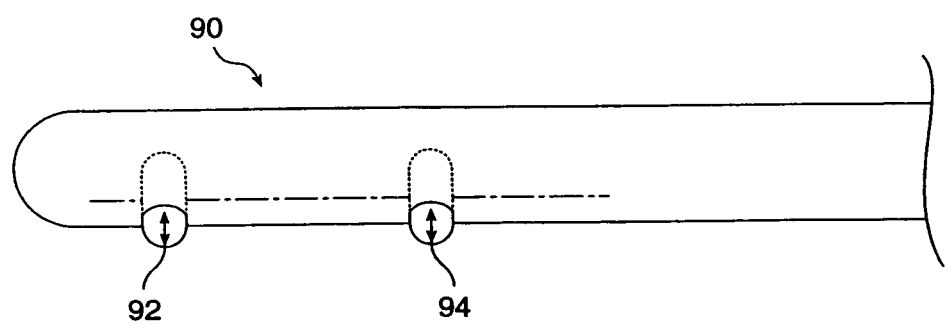
FIG. 14 illustrates a bipolar fascia contracting probe having roller electrodes to facilitate sweeping the probe over the fascia.

A wide variety of alternative electrode structures are also possible. Referring now to FIG. 14, a still further alternative embodiment of the present laparoscopic or endoscopic probe 90 has first and second partially enclosed roller electrodes 92, 94 for rolling against tissue surface without inadvertently engaging the surrounding tissues. More than two rollers may be used, with the polarity of the electrodes generally alternating (as can be understood with reference to FIGS. 10–121B). Such alternating electrodes may instead be defined by axial wires or ribbons in a straight configuration, or may curve in alternating spirals at the distal end of the probe. In some embodiments, the electrodes may be defined by the ends of coaxial tubes with insulating material between the tubes and over the outer tube.

While the shafts supporting the electrodes of the present invention are generally shown as straight structures, many of these embodiments may alternatively incorporate bends in the shafts between the proximal and distal ends. Alternatively, the shafts may be articulated to facilitate engaging the target tissue surface. Hence, the present invention encompasses not only straight shafts, but shafts which are slanted, angled, articulated, flexible, inflatable, or the like, to facilitate engaging a target tissue from the selected approach position.

Figure 15:
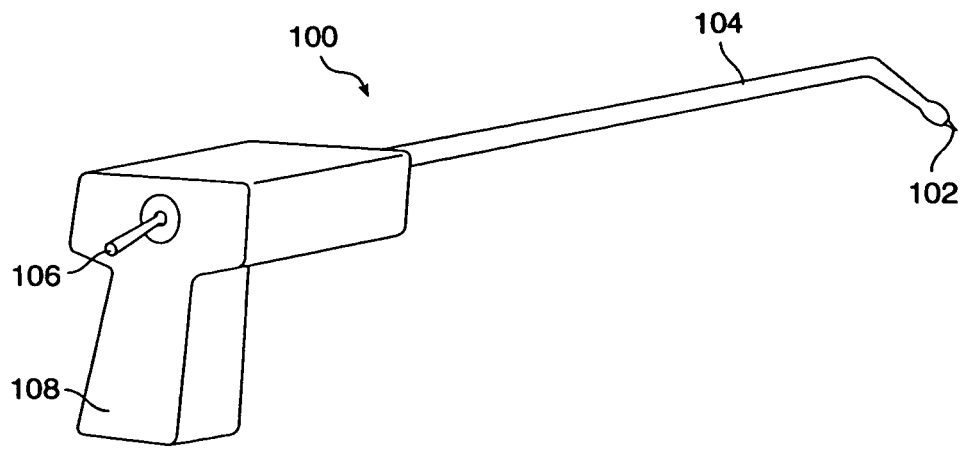
FIG. 15 illustrates a joystick actuated least invasive probe for penetrating through the vaginal mucosa to the mucosa/fascia interface, the endopelvic fascia surface, or the vesicle-vaginal space, the probe having an asymmetric handle to indicate the electrode orientation, according the principles of the present invention.

Referring now to FIG. 15, a least invasive probe 100 includes a distal needle 102 to facilitate inserting an articulated shaft 104 and access the fascia supporting the pelvic floor. The device will typically gain access to this treatment site by percutaneous insertion through the skin of the abdomen, through the wall of the vagina, or through the urethra. A joystick 106 manipulates articulated shaft 104, which can facilitate positioning the electrodes against the target tissue. Optionally, joystick 106 may also be used to direct needle 102 to penetrate the vagina mucosa or bladder surface.

Figure 15A:
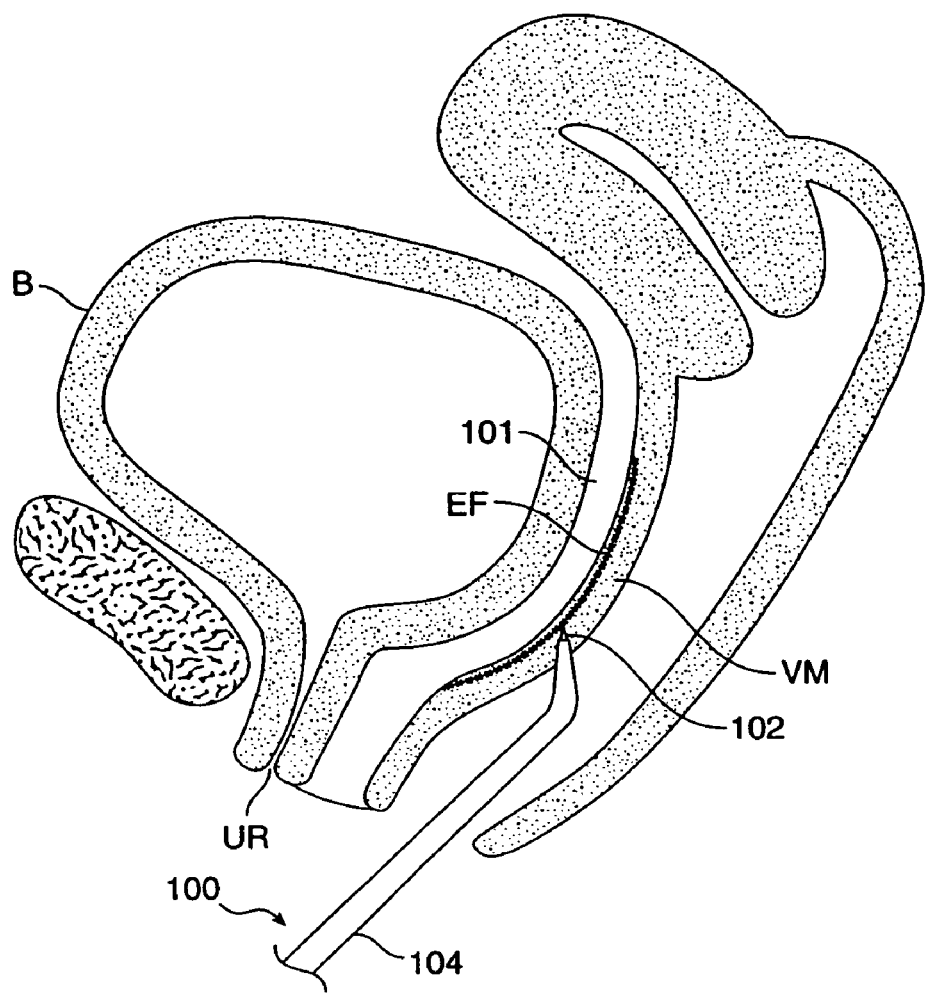
FIGS. 15A–15D illustrate least invasive methods for accessing the endopelvic fascia through the vaginal mucosa or the bladder wall.
Figure 15B:
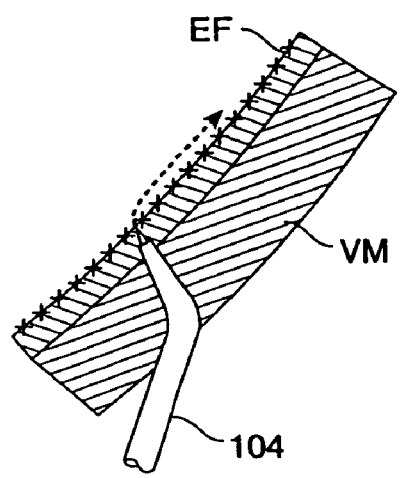
Figure 15C:
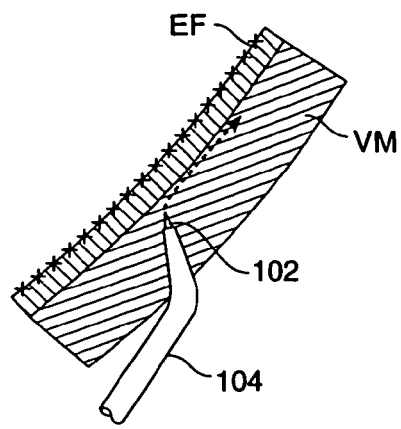

Methods for accessing endopelvic fascia EF using least invasive probe 100 are illustrated in FIGS. 15A–15C. Shaft 104 is inserted in the vagina and placed against the anterior surface. Needle 102 perforates the vaginal mucosa VM, optionally extending through endopelvic fascia EF to lay adjacent to (and in contact with) the endopelvic fascia between the endopelvic fascia and bladder B in the vesiclevaginal space 101. Alternatively, needle 102 may be directed through vaginal mucosa VM without perforating endopelvic fascia EF to lay in contact with the endopelvic fascia between the endopelvic fascia and the vaginal mucosa. In either case, once least invasive probe 100 has accessed endopelvic fascia EF, one or more electrodes will engage and heat the fascia to induce contraction. In some embodiments, a two-pronged needle probe could be used, with each needle having an electrode surface to facilitate bipolar resistive heating. Alternatively, the needle may be removed from the positioned least invasive probe 100 and replaced with a deployable electrode structure, as described hereinbelow.

Figure 15D:
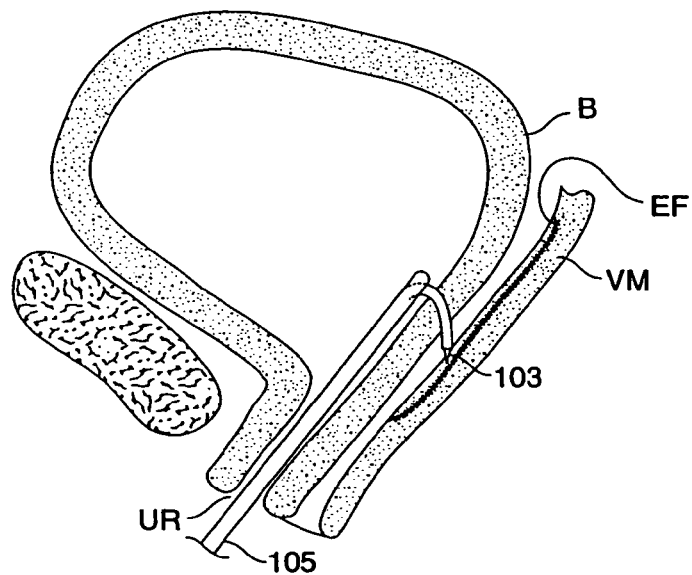

FIG. 15D illustrates a still further alternative method for accessing endopelvic fascia EF. In this embodiment, a cystoscope 105 is inserted through urethra UR into bladder B. A curved needle 103 punctures through the bladder wall with a retrograde orientation, the needle preferably being clear of the ureteral vesicle junctions and trigon. Curved needle 103 is again positioned in contact with endopelvic fascia EF on the anterior surface of the vagina. Such a method may make use of an off-the-shelf cystoscope.

Least invasive probe 100 will often be positioned using a remote imaging mechanism, typically in a fluoroscopically or ultrasonically directed procedure. To help ensure that the electrodes of least invasive probe 100 are properly oriented toward the target tissue, asymmetric handle 108 will often be rotationally affixed relative to the electrode. In some embodiments, electrodes may simply be positioned on the surface of articulatable shaft 104, on needle 102, or the like. However, to minimize the cross-section of 104 so as to facilitate percutaneous insertion, it will often be advantageous to include an electrode support structure which is deployable from the shaft once the electrodes are positioned adjacent the target surface. Such a deployable electrode structure may optionally be inserted through articulated shaft 104 after removal of needle 102, or may instead be incorporated into the distal end of articulated shaft 104.

Figure 16:
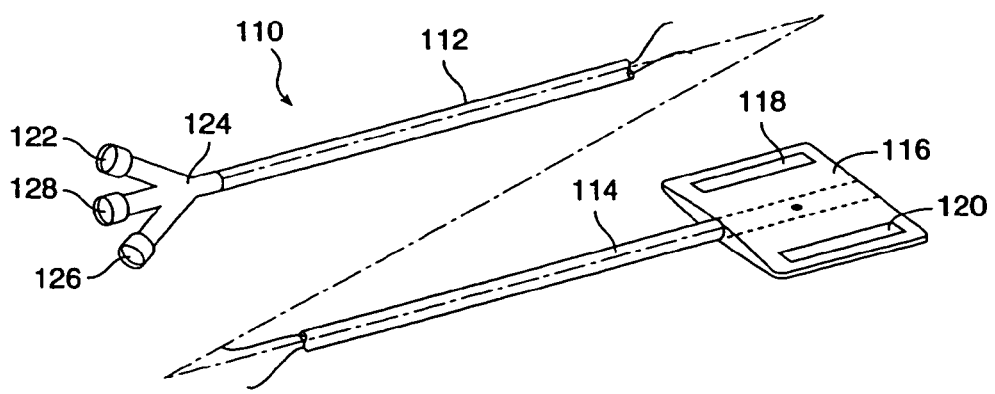
FIG. 16 illustrates an asymmetric least invasive probe having bipolar electrodes which are deployable by inflating a balloon.

An example of a deployable electrode structure is illustrated in FIG. 16. Balloon system 110 includes a shaft 112 having an angular position indicating line 114. Line 114 helps to indicate the orientation of a distal balloon 116 from the proximal end of the balloon system. In other words, line 114 allows the physician to verify that first and second balloon electrodes 118, 120 are properly oriented to engage the target tissue.

Figure 17A:
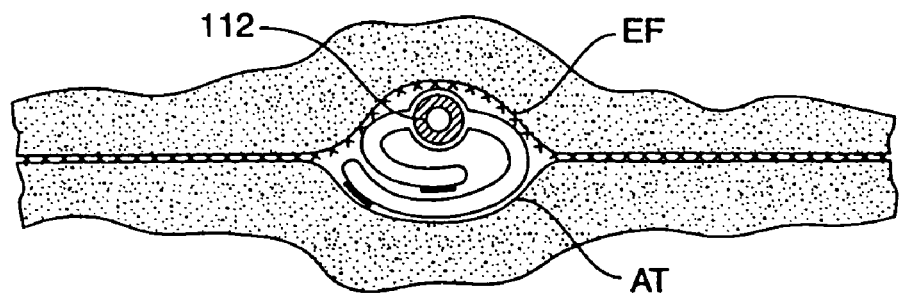
FIGS. 17A and 17B schematically illustrate self-orientation of the inflatable electrode assembly of the probe of FIG. 16.
Figure 17B:
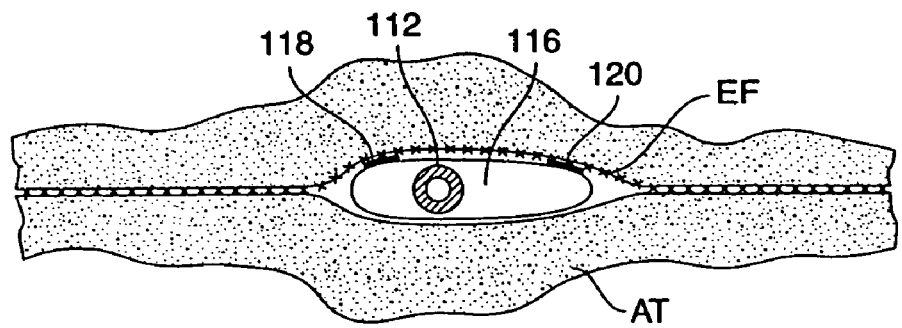

The use of balloon system 110 will be explained with reference to FIGS. 16, 17A and 17B. Balloon 116 is inserted between the endopelvic fascia EF and an adjacent tissue AT while the balloon system is in a narrow diameter configuration. In the narrow configuration, balloon 116 is deflated and the electrodes are disposed along shaft 112. Once the deflated balloon is at the desired location, the balloon may be roughly rotationally positioned with reference to line 114 on shaft 112. Balloon 116 can then be inflated through inflation port 122 on proximal balloon housing 124. As the balloon inflates, it separates endopelvic fascia EF from adjacent tissue AT. Additionally, as balloon 116 defines a substantially flat structure when inflated, it will tend to self-orient, so that first and second balloon electrodes 118, 120 engage the endopelvic fascia as shown in FIG. 17B.

In some embodiments, balloon 116 is bilaterally asymmetric to help verify the orientation of the deployed electrodes. The asymmetric feature of balloon 116 may comprise simple radiopaque or ultrasonically imageable markers, differing first and second electrode shapes, or the like. In the embodiment illustrated in FIG. 17B, the balloon is asymmetrically mounted to shaft 112. When viewed under fluoroscopy, ultrasound, or the like, this asymmetry helps verify the position and orientation of the electrodes.

Once the first and second balloon electrodes 118, 120 are positioned, the electrodes may be energized through electrical coupler 126. A third connector 128 on proximal housing 124 may be used for directing insertion of the balloon with a guidewire, gas insufflation, optical imaging, or the like.

Figure 18A:
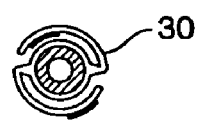
FIGS. 18A and 18B schematically illustrate the deployment of bipolar electrodes by inflating an asymmetric flat balloon with two different inflation media to radiographically verify the orientation of the electrodes.
Figure 18B:
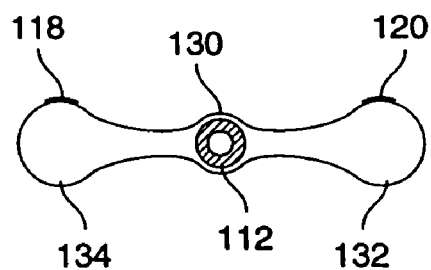

A wide variety of alternative balloon configurations may be used. For example, a two-part balloon 130 may be filled in-part with a radiopaque liquid 132, and in-part with a non-radiopaque gas or liquid 134, as can be understood with reference to FIGS. 18A and B. Under remote imaging, gas 134 and liquid 132 may be easily distinguished to verify the orientation of the electrodes.

Figure 19:
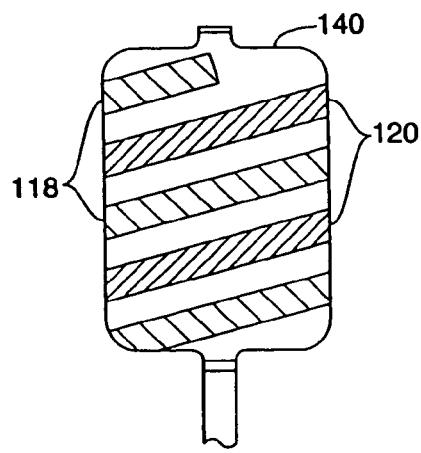
FIG. 19 illustrates the deployed state of an alternative balloon deployable electrode configuration for use with the least invasive probe of FIG. 15.

To enhance tissue contraction, it may be convenient to include a larger number of electrodes on the least invasive probe structure. Typically, these electrodes will be arranged as alternating bipolar structures, as can be understood with reference to FIGS. 19–20C. In some embodiments, the electrodes may be selectively energizable to vary the amount of contraction, and to direct the resistive heating to the target tissue without rotating the probe to a specific orientation. A barber pole balloon 140 having electrodes similar to the structure illustrated in FIG. 10 is shown in FIG. 19.

Figure 20A:
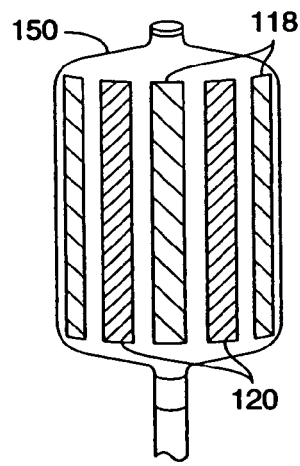
FIGS. 20A–20C schematically illustrate the deployed state of a balloon having alternating electrodes, and a method for its use to separate a fascia targeted for contraction from an adjacent tissue surface, after which the balloon is partially deflated for heating and contracting the fascia.
Figure 20B:
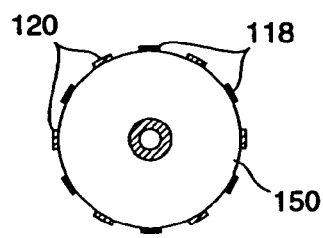
Figure 20C:
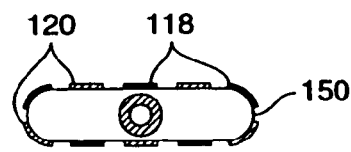
Figure 21A:
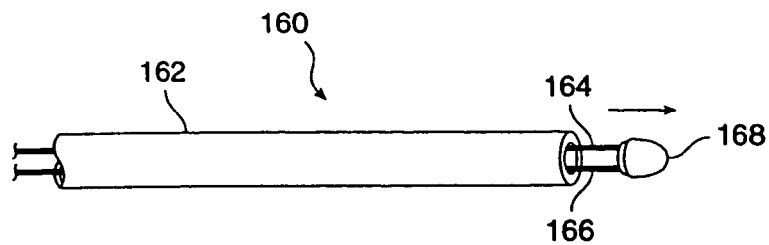
FIGS. 21A and 21B schematically illustrate bipolar electrodes which are supported along resilient elongate structures, in which the elongate structures are biased to separate the electrodes, for use with the least invasive probe of FIG. 15.
Figure 21B:
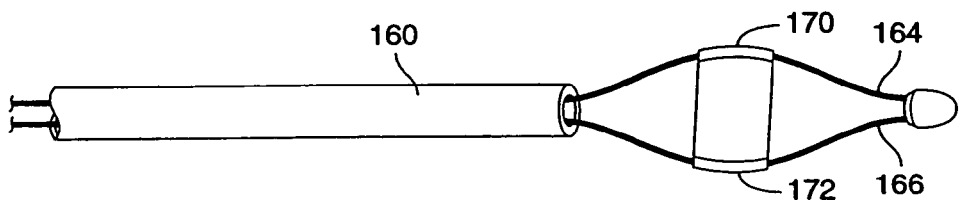
Figure 22A:
FIGS. 22A–22C schematically illustrate an alternative electrode deployment structure in which a pull-wire deflects elongate structures to deploy the electrodes.
Figure 22B:
Figure 22C:
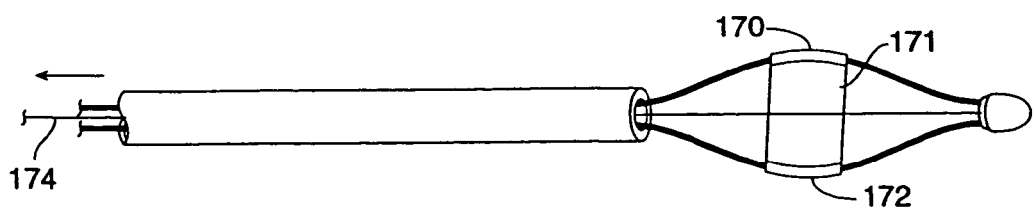

The balloon structures of the present invention need not necessarily be flat. For example, as illustrated in FIGS. 20A–C, a cylindrical balloon 150 may be inflated to separate the fascia from the adjacent tissue, and to enhance engagement of at least some of the electrodes against the fascia. By selectively energizing the electrodes which engage the endopelvic fascia, collateral damage to the adjacent tissues may be avoided. As illustrated in FIG. 20C, cylindrical balloon 150 may be partially deflated to avoid distention of the endopelvic fascia during heating, and thereby enhance contraction. Such partial deflation may also increase the number of electrodes which engage the target tissue.

Still further alternative deployable electrode support structures are illustrated in FIGS. 21A–23C. For example, a self-spreading electrode system 160 includes a sheath 162 which restrains elongate first and second electrode support structures 164, 166. Once the self-spreading system is positioned at the treatment site, sheath 162 is withdrawn proximally (or atraumatic tip 168 is advanced distally). The resilient support structures separate laterally when released from sheath 162, thereby deploying restrainable electrodes 170, 172. Optionally, a web 171 between the electrodes limits the separation of the electrodes to the desired distance. A similar deployable electrode structure may include elongate electrode support structures which are nominally straight, but which may be laterally displaced by a pull wire 174 to deploy the electrodes, as illustrated in FIGS. 22A–C.

Figure 23A:
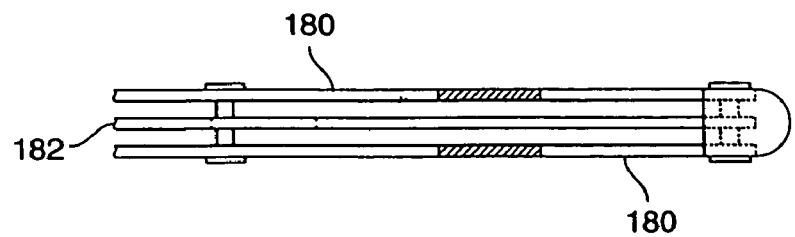
FIGS. 23A–23C schematically illustrate an electrode deployment structure in which a central member is tensioned to deflect the electrode support structures resiliently outwardly.
Figure 23B:
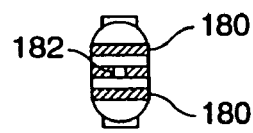
Figure 23C:
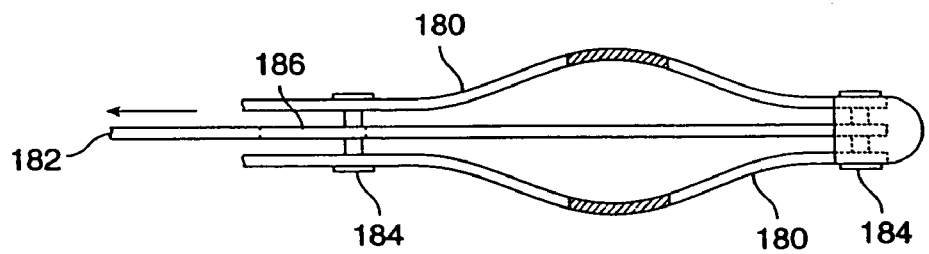

Still further alternative deployable electrode structures are possible. As illustrated in FIGS. 23A–C, lateral deployment of flat electrode support structures 180 may be effected by drawing a middle member 182 proximally. Fasteners 184 support the structures, and interact with a slot 186 in middle member 182 to limit axial movement of the middle member and thereby control the spacing between the deployed electrodes.

As explained above, thermocouples or other temperature sensors may be incorporated into the least invasive probes of the present invention, preferably between the bipolar electrodes. Feedback control may alternatively be provided by monitoring the energizing circuit, as was also explained above. Those of skill in the art will recognize that balloon electrode support structures may make use of single lumen, or multiple lumen shafts for inflation, energizing wires, temperature sensing feedback, guidewires, gas or fluid insertion, and the like.

Figure 24:
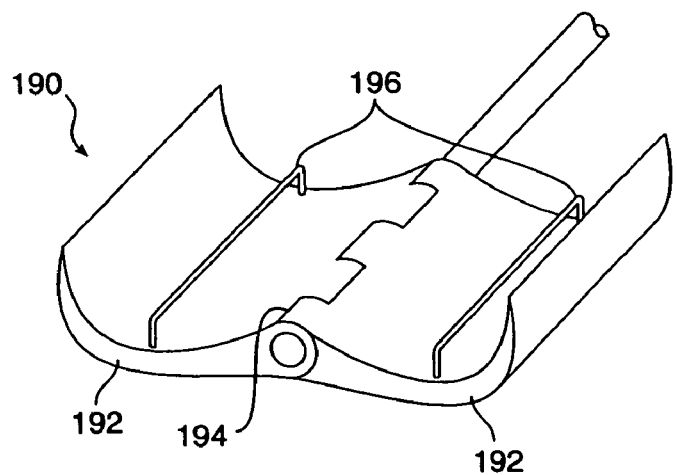
FIG. 24 is a perspective view of an alternative probe for shrinking endopelvic fascia and other collagenated tissues, in which the probe includes a grasper which reduces tension in the region of tissue to be contracted to enhance shrinkage.

A grasping probe 190 is illustrated in FIG. 24. Grasping probe 190 includes a pair of arms 192 which rotate about a hinge 194. Electrodes 196 are disposed between arms 192 and oriented so as to engage the surface of the tissue which is grasped by the arms.

Figure 25A:
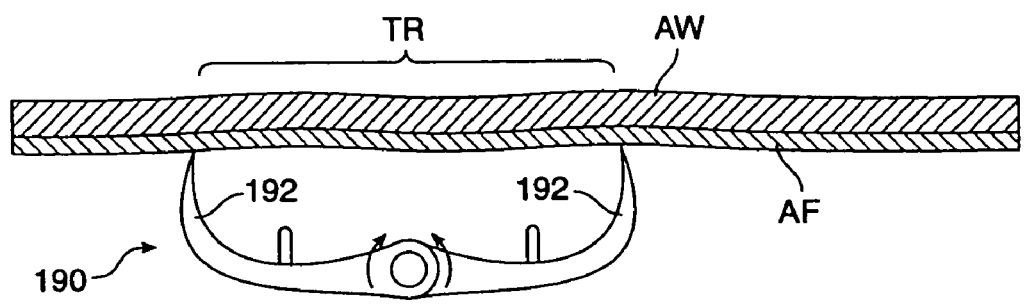
FIGS. 25A and 25B schematically illustrate a method for using the probe of FIG. 24 by grasping the target tissue and drawing a region of the target tissue inward to reduce tension in the engaged tissue, and thereby enhance shrinkage.
Figure 25B:
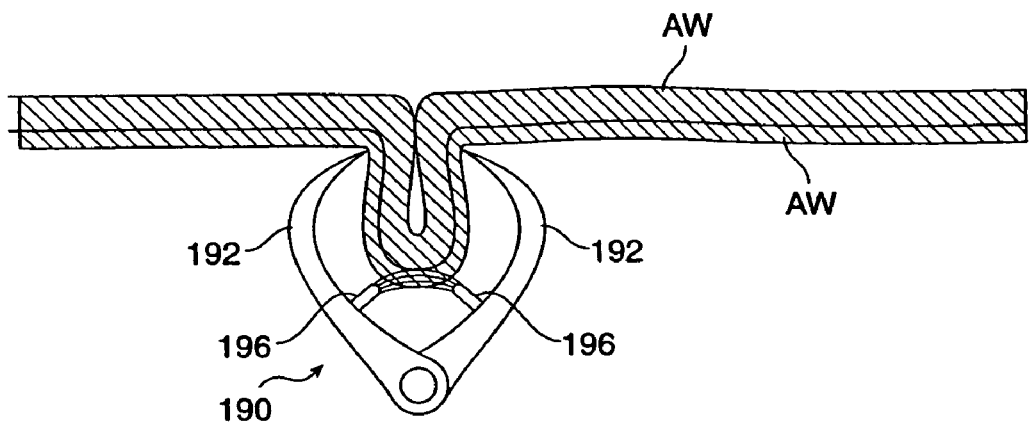

A method for using grasping probe 190 is illustrated in FIGS. 25A and 25B. In this embodiment, arms 192 engage abdominal fascia AF of abdominal wall AW. Arms 192 grasp and draw a region of the tissue TR inward so as to reduce tension within the grasped region. Electrodes 196 engage abdominal fascia AF within the tissue region TR, and a current flux is directed between these electrodes to heat and shrink the abdominal fascia.

Preliminary work in connection with the present invention has shown that a wall stress of 1.3 lbs. per linear inch can limit the shrinkage of some fascia to about 20%, rather than the 40% to 50% shrinkage observed when that fascial tissue is not in tension. Hence, the method illustrated in FIGS. 25A and 25B will find a variety of applications for shrinking tissues which would otherwise be under tension during the procedure. Specifically, the illustrated method may be used during abdominoplasty (sometimes referred to as a "tummy tuck") to selectively shrink the abdominal wall. By reducing tension in the abdominal tissues, the shrinkage provided from the application of heating energy can be increased significantly. Alternatively, the amount of area treated to provide a particular reduction in length of the fascia can be minimized. If sufficient tissue is treated using such a method, the waistline of the patient could be reduced by several inches.

Grasping probe 190 may also be used in a wide variety of procedures, and a variety of grasping structures might be used, generally by grasping a region of the tissue to be treated and pulling the region inward to eliminate and/or reduce tension in the grasped region. The grasped tissue should be free to shrink while grasped by the probe, and the fascia should be exposed for contact with the bipolar electrodes, or otherwise in a position to be heated by a heating element. In some embodiments, the grasped tissue may be heated by a laser, a monopolar radiofrequency electrode, a microwave antennae, focused ultrasound transducer, a heated probe surface, or the like. The grasped fascia may generally be heated by any heating element, and will shrink to a greater extent than would otherwise result from heating tensioned fascia (or other collagenated tissue).

Grasping probe 190 may include a wide variety of alternative grasping structures. In some embodiments, the ends of arms 192 may include protruding points to penetrate into and more firmly grip the fascia. A vacuum mechanism may be used to grasp the tissue region TR between the arms, or discrete vacuum ports on each arm might be used. Arms 192 might slide (rather than pivot) relative to each other, and electrodes 196 may be affixed to a single structure to maintain a predetermined interelectrode separation, and to limit tissue heating depth, as described above.

Figure 26:
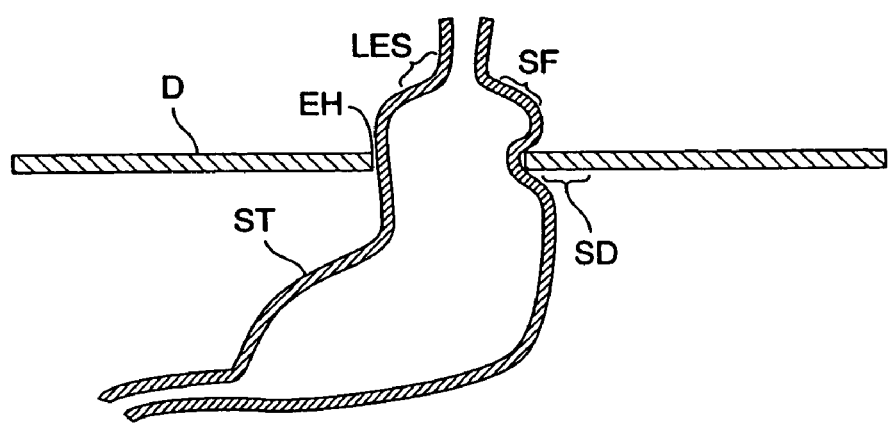
FIGS. 26–26C are cross-sectional views of a patient suffering from a hiatal hernia showing a method for treatment using the probes of the present invention.
Figure 27:
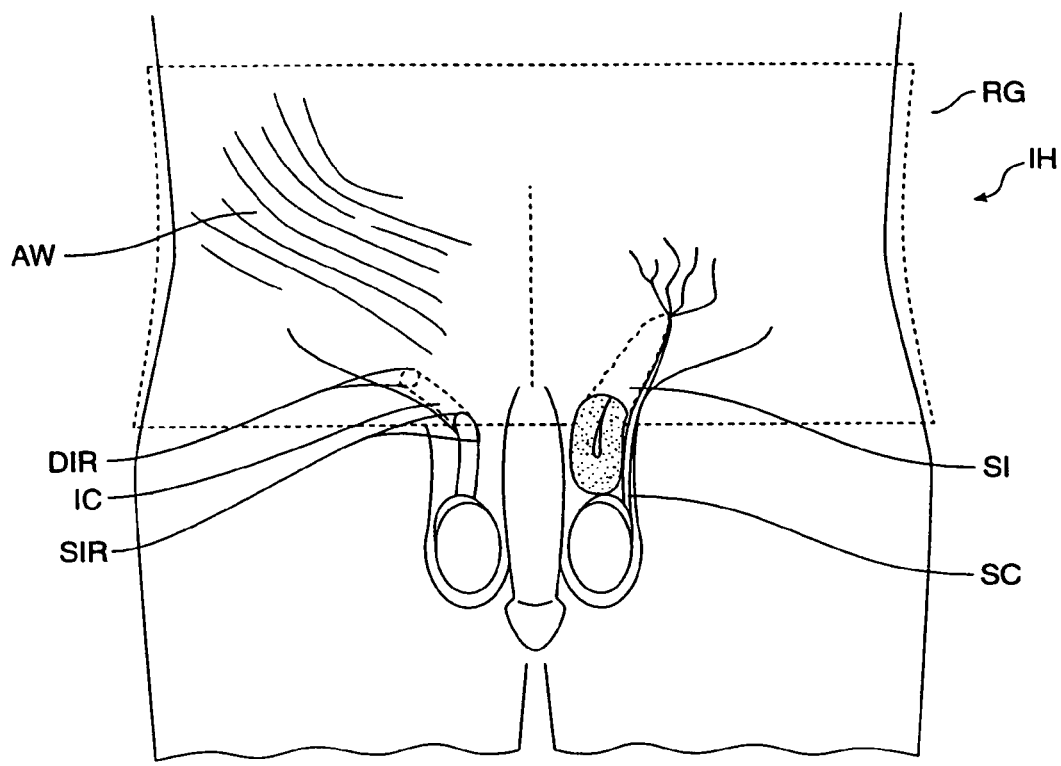
FIG. 27 illustrates a patient suffering from an inguinal hernia, and identifies regions for treating the inguinal hernia using the methods of the present invention.

The devices and methods of the present invention will find particularly advantageous applications for treatment of hernias, as can be generally understood with reference to FIGS. 26 and 27. In FIG. 26, a portion of a stomach ST protrudes through an enlarged esophageal hiatus EH of a diaphragm D. This can lead to severe reflux, in which the acidic stomach juices are persistently regurgitated, eroding the wall of the esophagus and causing a burning pain. These symptoms are often aggravated by a defective lower esophageal sphincter LES. While such conditions may be treated using known methods, particularly using laparoscopic Nissen fundoplication, these surgical procedures require significant amounts of surgical experience and skill to be successful. Lack of experience in these specialized procedures can lead to severe complications, including pneumothorax, dysphagia, recurrent reflux, and loss of motility, thereby making it difficult and/or impossible to eat. Hiatal hernias may include a tear in the diaphragm of between 1 and 5 cm adjacent hiatus EH.

To overcome these disadvantages, the hiatal hernia illustrated in FIG. 26 may instead be treated by selectively shrinking the fascia of diaphragm D. Using the methods and devices of the present invention, the diameter of esophageal hiatus EH can be decreased so that the diaphragm properly contains the stomach. Specifically, stomach ST is repositioned below diaphragm D, and grasping probe 190 (illustrated in FIG. 24) grasps the upper or lower surface of diaphragm D adjacent the esophageal hiatus. A portion of the diaphragm adjacent the esophageal hiatus is drawn inward, preferably circumferentially so as to decrease the size of the hiatus. The fascia of diaphragm D may then be heated and contracted to prevent stomach ST from again protruding through the diaphragm. Alternatively, probe 10 (illustrated in FIG. 1), or any of the alternative tissue contracting structures described herein, might be used, particularly where diaphragm D is not under tension during treatment.

To improve the competence of lower esophageal sphincter LES, fascia adjacent and external to the sphincter may be treated to close the valve more effectively. In some embodiments, such as where a Nissen procedure would normally be indicated, or where a reinforcing patch might otherwise be placed over the defect to prevent recurrence of the hiatal hernia, the fascial covering of the top of the stomach SF and the corresponding surface of the diaphragm SD may be treated to promote the formation of an adhesion between these surfaces (which will engage each other once stomach ST is properly positioned below diaphragm D). Such an adhesion would decrease the likelihood of recurrence of the hiatal hernia, and may generally reinforce the defect.

Figure 26A:
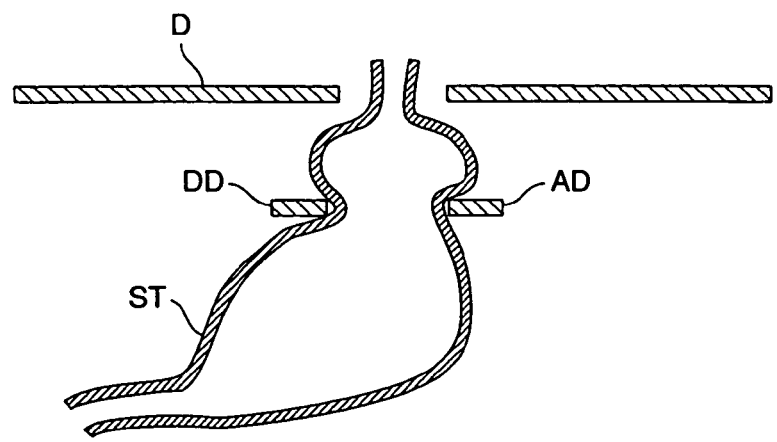
Figure 26B:
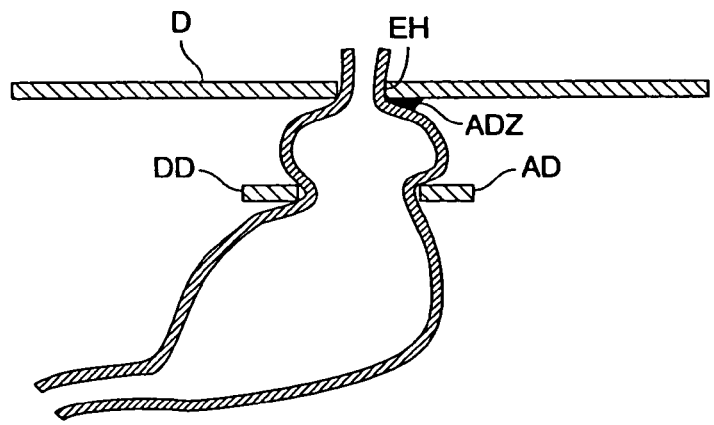
Figure 26C:
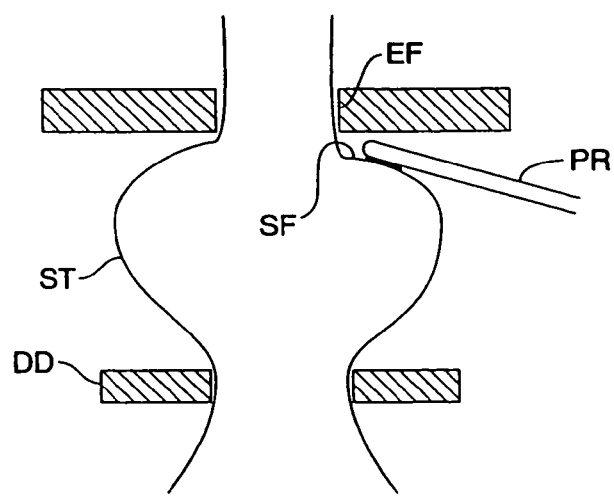

A method for treating a hiatal hernia by forming a reinforcing adhesion can be understood with reference to FIGS. 26A–26C. Stomach ST is dissected from the surrounding diaphragm D, with a dissected portion of the diaphragm DD often remaining affixed to the stomach by adhesions AD, as illustrated in FIG. 26A. The resulting enlarged hole in diaphragm D is contracted by shrinking the collagenated diaphragm about the hole, as described above and as illustrated in FIG. 26B. To secure stomach ST below the contracted diaphragm, the adjacent surfaces of the stomach and the diaphragm are treated to promote formation of an adhesion ADZ connecting these tissues. The dissected diaphragm segment DD about stomach ST may be removed to reduce necking, or may be left in place. A probe PR treating a superior surface of stomach ST is illustrated in FIG. 26C. It should be noted that the resulting 2 treated, opposed surfaces will generally develop adhesions, while the treatment of only one of the opposed surfaces will not reliably promote adhesion formation. Once diaphragm D is contracted to properly size esophageal hiatus EH, and once adhesion ADZ connects the diaphragm to the stomach, reoccurrence of the hiatal hernia is substantially inhibited.

The methods and devices of the present invention are also suitable for treatment of inguinal or abdominal hernias, as illustrated in FIG. 27. In inguinal hernia IH, a portion of the small intestine SI protrudes through the inguinal canal IC adjacent the spermatic cord SC. Using the methods of the present invention, the abdominal wall adjacent the deep inguinal ring DIR and/or adjacent the superficial inguinal ring SIR may be selectively contracted about the spermatic cord once the small intestine SI has been pushed back into the abdominal cavity. Selective shrinking of the fascial tissue about the spermatic cord will allow the fascial tissue to properly contain the abdominal organs, often without having to resort to sutures, patches, and the like. Where the abdominal wall is not torn adjacent the hernia, treatment will often be possible without grasping and drawing the tissue inward, as the stretched tissue should not be under tension after the herniated bowel has been repositioned within the abdomen. Work in connection with the present invention has found that even hernias resulting in small tears of the fascial tissue can be corrected by shrinking using a laparoscopic probe similar to that illustrated in FIG. 1. Preferably, such tears will be less than 2 cm in length, ideally being under 1 cm. In some embodiments, particularly where extended tears of the fascial tissue have been found, the selective shrinking of the present invention may be combined with suturing, patches, and other known hernia repair techniques. Once again, where the abdominal wall is under tension during the treatment procedure, a grasping probe, such as that illustrated in FIG. 24, might be used to enhance the effective contraction of the abdominal wall.

Fascial tissue, once shrunk using the methods of the present invention, has nearly 20 times the strength needed to contain the intestines in place. Nonetheless, to prevent the treated tissue from stretching or tearing during the healing process, a retention girdle RG may be worn. Retention girdle RG may help contain the tremendous forces generated by coughing sneezing, and the like, particularly for a period of about 8 weeks after a selectively shrinking of the fascia.

The present invention optionally relies on inducing controlled shrinkage or contraction of a tissue structure which comprises or supports portions of the patient's urethra. The tissue structure will be one that is responsible in some manner for control of urination and where contraction of the tissue structure will have the effect of reducing urinary leakage. Exemplary tissue structures include the urethral wall, the bladder neck, the bladder, the urethra, bladder suspension ligaments, the sphincter, pelvic ligaments, pelvic floor muscles, fascia, and the like. In one exemplary embodiment, a portion of the urethral wall at or near the urethral sling is heated to contract tissue and create a kink or crease in the wall which provides a preferential closure site for the urethra. In effect, it becomes easier for the patient's weakened tissue support structures to close the urethra and maintain continence. In another exemplary embodiment, the supporting tissues and ligaments are shortened to at least partially reverse the stretching and weakening that has resulted from pregnancy or other patient trauma. By selectively contracting one or more of the pubococcygeal, iliococcygeal and/or detrusor muscles, support of the ureter and urinary sphincter can be substantially improved.

Tissue contraction results from controlled heating of the tissue by affecting the collagen molecules of the tissue. Contraction may occur as a result of heat-induced uncoiling as the collagen β-pleated structure and subsequent re-entwinement as the collagen returns to body temperature. By maintaining the times and temperatures set forth below, significant tissue contraction can be achieved without substantial tissue necrosis.

While the remaining description is specifically directed at an energy-applying probe introduced through the urethra of a female patient, it will be appreciated that the methods of the present invention can be performed with a variety of devices and systems designed to deliver energy to tissue target sites resulting in heating of the tissue and selective contraction of tissue support structures. The temperature of the target tissue structure can here be raised to a value in the range from 70° C. to 95° C., for a time sufficient to effect the desired tissue shrinkage. In these embodiments, the temperature will be raised from ½ second to 4 minutes, optionally being from 0.5 minutes to 4 minutes and often from 1 minute to 2 minutes. The total amount of energy delivered will depend in part on which tissue structure is being treated as well as the specific temperature and time selected for the protocol. The power delivered will often be in the range from 1 W to 20 W, usually from 2 W to 5 W.

Figure 28:
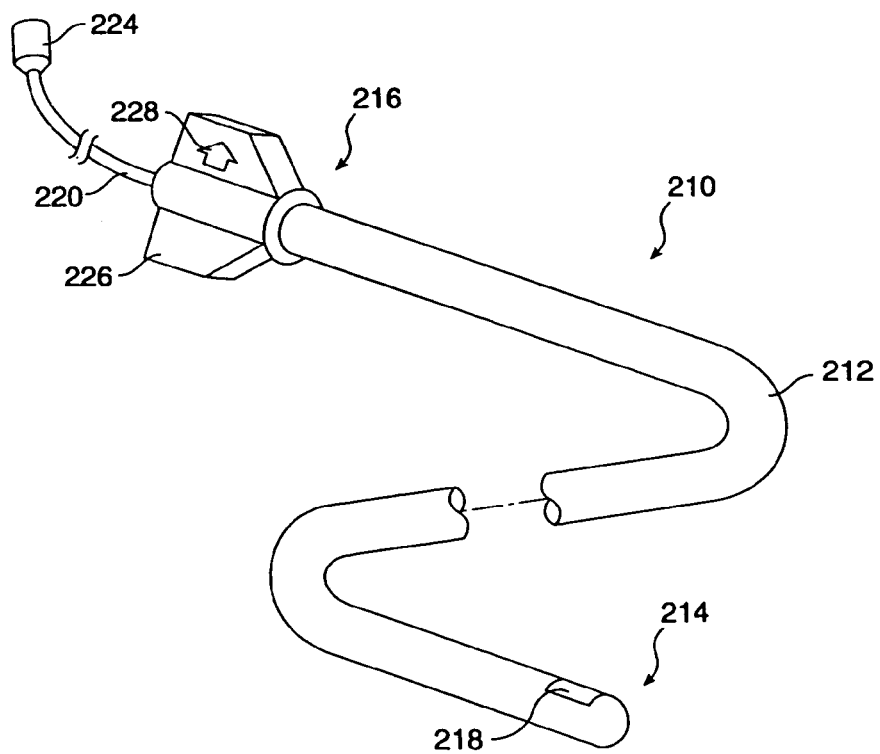
FIG. 28 is a perspective view of an exemplary electrosurgical probe constructed in accordance with the principles of the present invention.
Figure 28A:
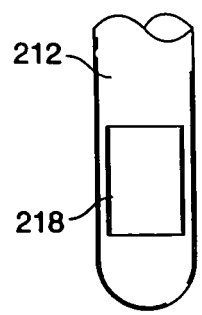
FIGS. 28A–28D illustrate alternative electrode configurations for the probe of FIG. 28.

Referring now to FIG. 28, a heat-applying probe 210 comprises a probe body 212 having a distal end 214 and a proximal end 216. An electrode 218 is disposed near the distal end 214 of the probe body 212 and is connected via electrically conductive wires (not shown) extending the length of the body and out through a connector cable 220 having a plug 224 at its proximal end. Usually, a proximal handle or hub 226 is provided at the proximal end 216 of the probe body 212. Conveniently, the hub 226 may include an arrow 228 indicating alignment of the probe hub with the asymmetrically mounted electrode 218.

Figure 30:
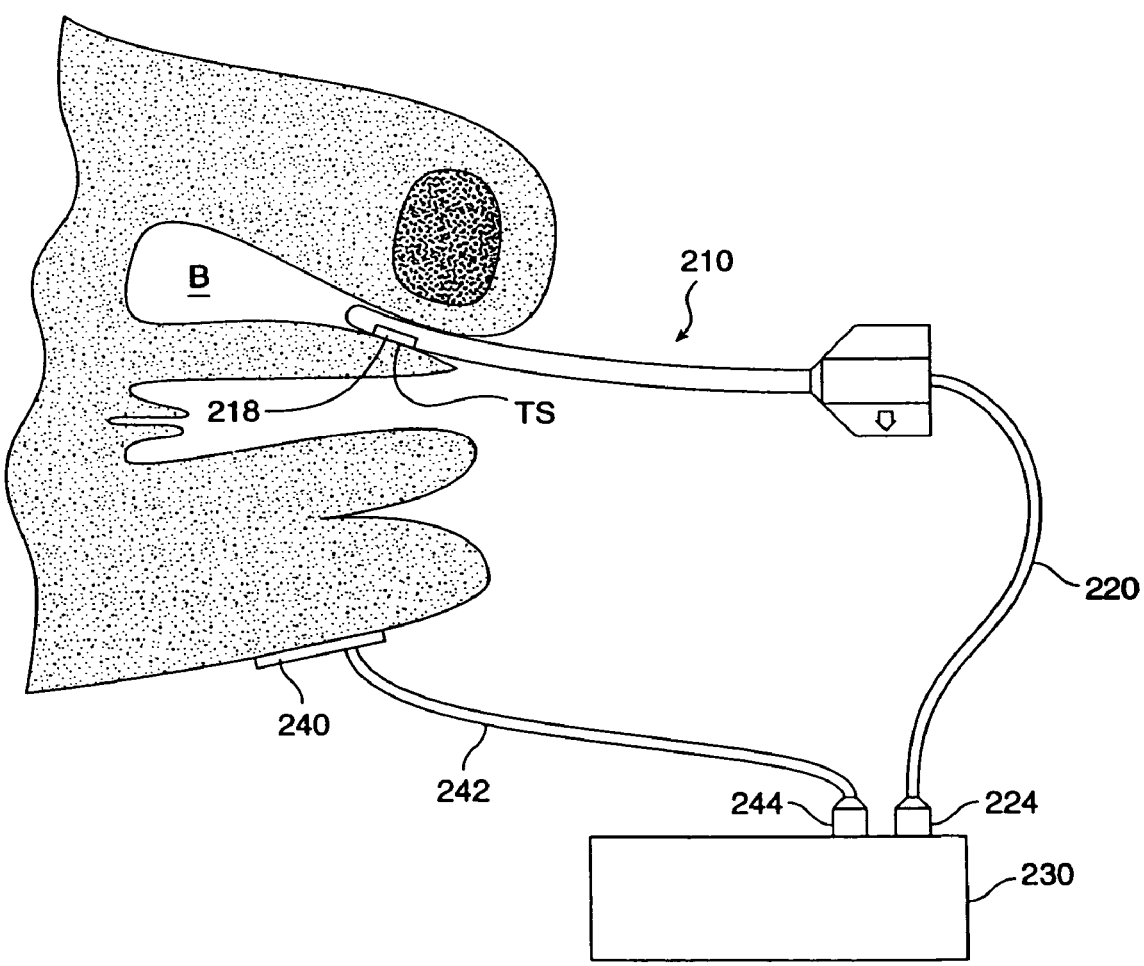
FIG. 30 illustrates a system comprising the probe of FIG. 28 and a power supply performing a procedure in a patient's urethra.

The electrode 218 is intended for delivering RF energy when attached to a power supply 230 (FIG. 30) connected through the plug 224 in cable 220. As shown in FIGS. 28 and 30, the single electrode 218 is intended for monopolar operation. The electrode 218 may be formed from many conventional electrically conductive electrode materials, such as stainless steel, platinum, conductive plastic, or the like. The probe may be formed from any conventional medical catheter or probe material, including organic polymers, ceramics, or the like. Usually, the probe body will be sufficiently flexible to be introduced through the urethra with minimal discomfort, but it would also be possible to utilize substantially rigid probes as well.

Figure 28B:
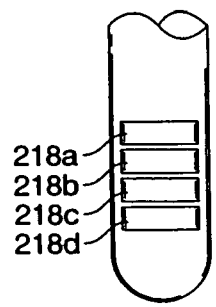
Figure 28C:
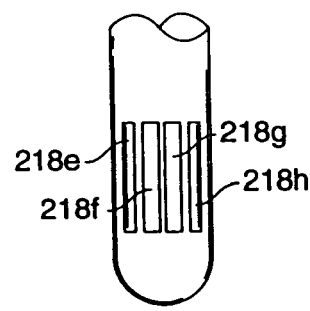

The energy-applying probe 210 could also be adapted for bipolar operation by including two or more isolated electrode surfaces near its proximal end 218 (with electrically isolated conductors to each of the electrode surfaces). As shown in FIG. 28B, a plurality of axially spaced-apart electrode surfaces 218a, 218b, 218c, and 218d could be connected with an alternating polarity. Alternatively, as shown in FIG. 28C, a plurality of circumferentially spaced-apart electrodes 218e, 218f, 218g, and 218h could also be connected with alternating polarity. Usually, each of the electrodes will be connected through the probe body 212 by a single isolated wire or other conductor, terminating in the connector plug 224. Thus, the multiple electrode configurations of FIGS. 28B and 28C can be operated either in a monopolar or bipolar fashion, depending on how the power supply is configured.

Figure 28D:
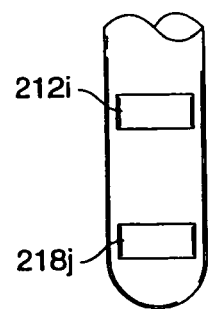

A particular electrode configuration including a pair of axially spaced-apart electrodes 218i and 218j is illustrated in FIG. 28D. This electrode configuration is intended for treating the urethral wall at locations immediately upstream and downstream of the urethral sling. Typically, the electrodes will be spaced-apart by distance in the range from 1 mm to 5 mm, preferably from 1.5 mm to 3 mm.

In all the electrode configurations of FIGS. 28–28D, the total electrode area will usually be in the range from 1 mm$^2$ to 10 mm$^2$, preferably from 2 mm$^2$ to 6 mm$^2$. Moreover, the electrodes will be configured to reduce or eliminate electrical current concentrations when operating in a radio frequency mode. Usually, the electrode surfaces will be relatively smooth, and the edges will be insulated or protected by the adjacent probe body 212. In this way, the electric field or flux emanating from the electrodes 218 will be relatively uniform, resulting in generally even heating of the tissue which is contacted by the electrode.

Figure 29:
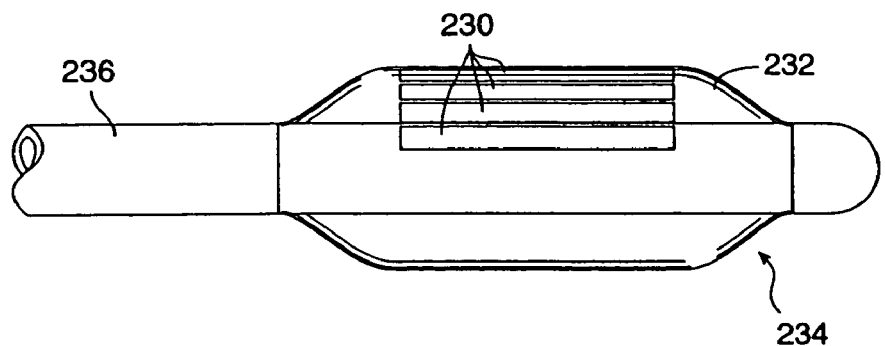
FIG. 29 illustrates a distal probe tip having an expandable balloon carrying an electrode array.

A further exemplary electrode embodiment is shown in FIG. 29. There, a plurality of circumferentially spaced-apart electrodes 230 are mounted on an inflatable balloon 232 at the distal end 234 of an energy-applying probe 236. Each of the electrodes 230 will be connected to a single or to multiple conductors running to the proximal end (not shown) of the energy-applying probe 236, in a manner similar to that illustrated for probe 210. By mounting the electrodes 230 on a radially expandable balloon or other expansion member (e.g., an expandable cage), the electrodes can be firmly contacted against an interior surface of the urethra. Moreover, the contact can be maintained as the urethral wall expands or contracts, depending on how the energy is applied.

Referring now to FIG. 30, use of the energy-applying probe 210 for treating a target site TS in a urethra draining bladder B is illustrated. The probe 210 is inserted so that electrode 218 contacts the target site TS, which is typically adjacent the urethral sling. The electrode may be positioned based on ultrasonic imaging, fluoroscopic imaging, or the like. Alternatively, the probe may be inserted to a known depth using a scale formed on the exterior of the probe (not shown). After properly positioning the electrode 218, RF energy is applied from power supply 230 typically at a level in the range from 1 W to 20 W, usually from 2 W to 5 W. As illustrated, the electrode 218 is a monopolar electrode, and a counter electrode 240 will be attached to an external portion of the patient's skin. The counter electrode is connected to the power supply 230 by an appropriate cable 242 and plug 244. Energy is applied until the tissue temperature is reached and maintained for a desired amount of time. Optionally, a temperature sensor can be provided on the probe 210, and feedback control of the amount of energy being applied can be implemented. For example, a thermal couple, a thermistor, or other temperature sensor can be mounted adjacent to or within the electrode 218. Alternatively, a penetrating element (not shown) can be provided on the probe to enter beneath the surface of the urethral wall by a pre-selected distance to measure internal tissue temperature. Other known temperature control techniques could also be utilized.

Figure 31:
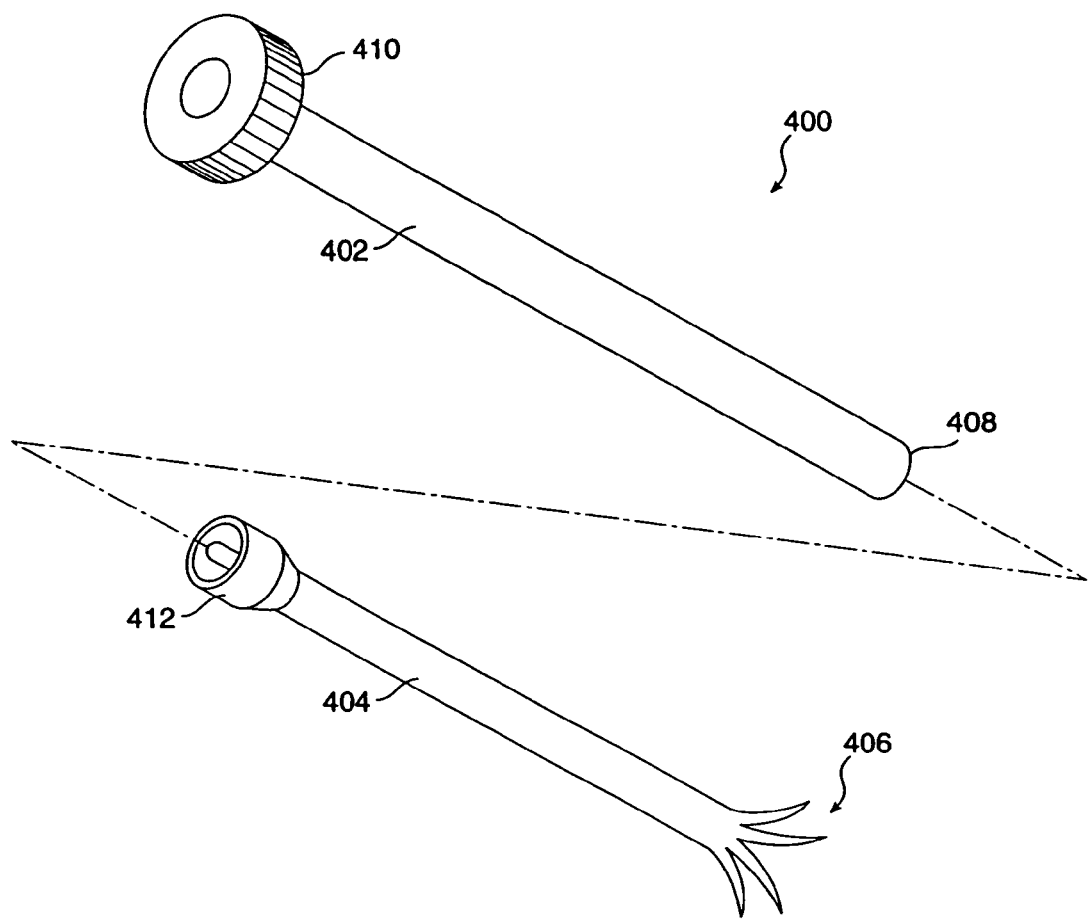
FIG. 31 illustrates a second exemplary electrosurgical probe constructed in accordance with the principles of the present invention.
Figure 32:
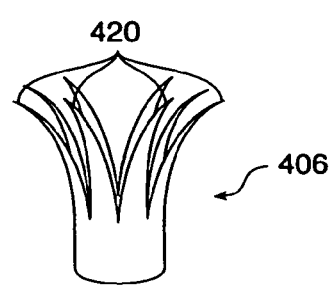
FIG. 32 is a detailed distal end view of the probe of FIG. 31.
Figure 33:
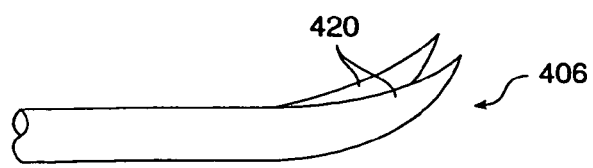
FIG. 33 is a detailed distal side view of the probe of FIG. 31.
Figure 34:
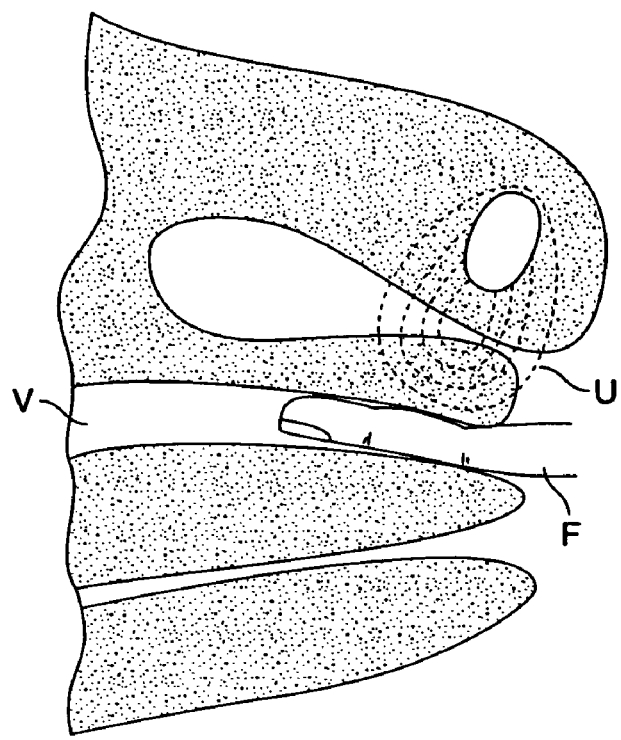
FIGS. 34–37 illustrate the use of the probe of FIGS. 31–33 in performing a procedure in a patient's vagina.
Figure 35:
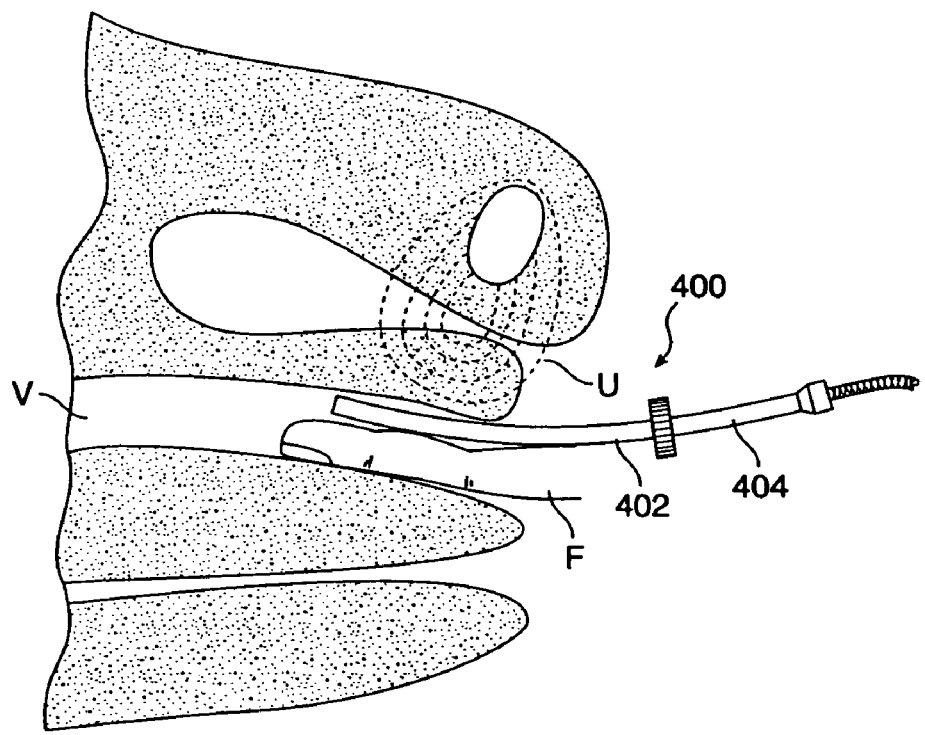

Referring now to FIGS. 31–33, a heat-applying probe 400 comprises a probe body having a sheath component 402 and an electrode rod component 404. The electrode rod 404 is reciprocatably mounted in a lumen of the sheath 403 so that a distal electrode array 406 on the rod 404 may be retracted and extended into and from the distal end 408 of the sheath 402. A proximal handle 410 is provided on the sheath, and a proximal connector 412 is provided on the electrode rod component 404.

The electrode array 406, as illustrated, includes four individual electrode tips 420 each of which has a sharpened distal end suitable for penetrating into tissue, particularly for transmucosal penetration through the vaginal wall into the tissue structures which support the urethra or urinary sphincter. The electrode tips 420 are sufficiently resilient so that they will be radially contracted when the rod 404 is withdrawn proximally into the sheath 408. The electrode tips 420 will resiliently expand from the sheath when the electrode rod component 404 is advanced distally when the sheath 408 is positioned near the tissue target site, as discussed in more detail below. As illustrated, the electrode tips 420 are commonly connected to a single plug in the connector 412. Thus, the probe 400 is only suitable for monopolar operation. It will be appreciated, however, that the multiple electrode tips 420 could be connected through separate, isolated conductors within the rod 404 and further be connected through multiple pins in the connector 412. Thus, the probe 400 could readily be adapted for bipolar operation. Usually, all components of the probe will be insulated, other than the electrode tips 420. Alternatively, some other portion of the rod 404 or sheath 402 could be formed from electrically conductive material and utilized as a common or indifferent electrode so that the probe could be utilized in a bipolar manner. A variety of such modifications would be possible with the basic probe design.

Figure 36:
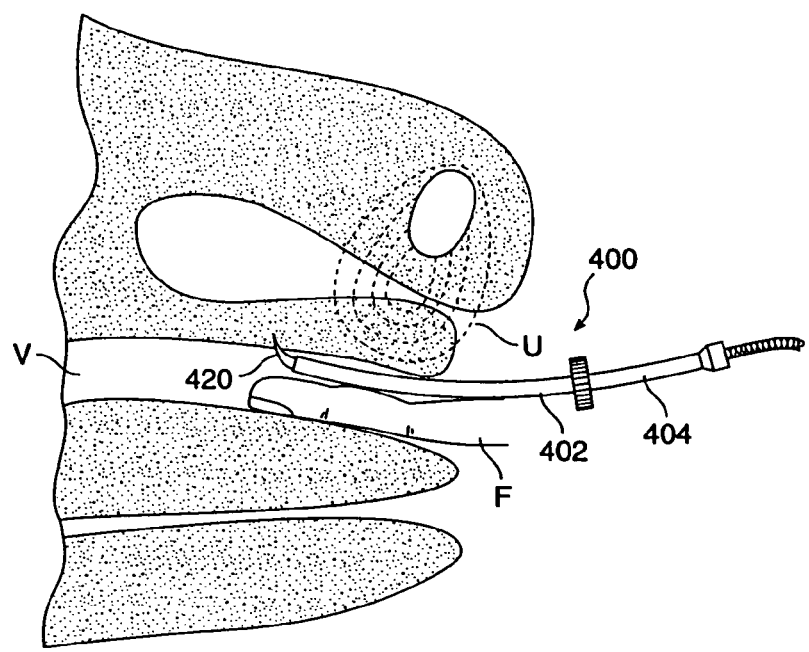
Figure 37:
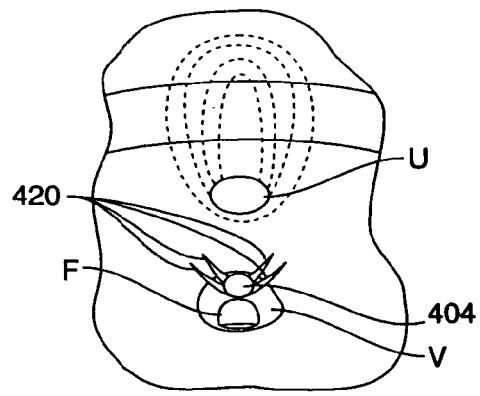

Referring now to FIGS. 34–37, use of probe 400 for contracting tissue ligaments which support the urethra in the region of the urethral sling will be described. Initially, the treating physician manually examines the vagina V to locate the region within the vagina beneath the urethral sling. The probe 400 is then introduced into the vagina. Conveniently, the physician may manually locate the probe, again by feeling the region which is supported by the urethral sling. After the sheath 402 of the probe 400 is properly positioned, the rod component 404 will be distally advanced so that the electrode tips 420 are penetrated into the tissue which supports the urethra, typically the pubococcygeal muscles, iliococcygeal muscles or the detrusor muscle as illustrated in FIGS. 36 and 37. The physician will continue to use a finger F to hold the probe against the vaginal wall to facilitate penetration of the electrode tips 420. RF energy can then be applied through the probe in order to heat the target tissue to temperatures and for time periods within the ranges set forth above. The supporting tissues are thus contracted in order to reduce urinary leakage and enhance patient continence.

The procedures of the present invention result in bulking and buttressing of the supporting tissue structures as the tissue heal. This result is in addition to the tissue contraction, with both the contraction and tissue bulking/buttressing acting to enhance patient continence.

Figure 38:
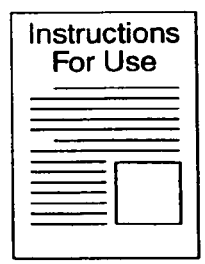
FIG. 38 schematically illustrates a kit including a laparoscopic tissue contraction probe, packaged together with pointed instructions for its use to contract tissue as a treatment for urinary incontinence.
Figure 38:
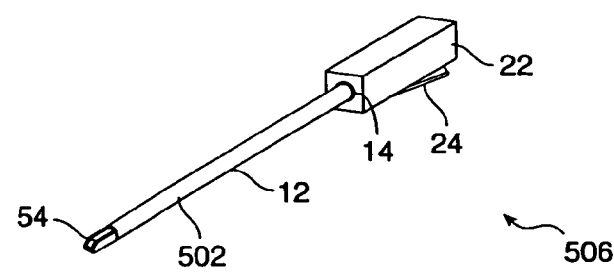

Referring now to FIG. 38, a kit 500 includes a tissue contracting probe 502 and instructions for its use 504. Contracting probe 502 and instructions 504 are disposed in packaging 506. Contracting probe 502 here includes a structure similar to probe 10 of FIG. 1, but has a radially ended tip 54 to facilitate laparoscopically engaging the electrode wires against both laterally and axially oriented tissues. Instructions 504 will often set forth the steps of one or more of the methods described herein above for treating urinary incontinence. Additional elements of the above-described systems may also be included in packaging 506, or may alternatively be packaged separately.

Instructions 504 will often comprise printed material, and may be found in whole or in part on packaging 506. Alternatively, instructions 504 may be in the form of a recording disk or other computer-readable data, a video tape, a sound recording, or the like.

The present invention further encompasses methods for teaching the above-described methods by demonstrating the methods of the present invention on patients, animals, physical or computer models, and the like.

While the exemplary embodiment has been described in some detail, by way of illustration and for clarity of understanding, various modifications, adaptations, and changes will be obvious to those of skill in the art. Therefore, the scope of the present invention is limited solely by the appended claims.

What is claimed is:

1. A method for inhibiting incontinence of a patient, the method comprising:
   advancing an electrode of a probe into a collagenous target tissue, the electrode comprising a needle electrode; and
   transmitting energy from an energy-directing element of the probe to the collagenous target tissue, the collagenous target tissue comprising or supporting a urethra of the patient, the energy being transmitted so as to induce a healing response in the collagenous target tissue, the healing response comprising bulking or buttressing of the collagenous target tissue and the bulking or buttressing of the collagenous target tissue inhibiting the incontinence, wherein the energy comprises RF energy delivered with the electrode of the probe.

2. The method of claim 1, wherein the energy heats the collagenous target tissue sufficiently to induce shrinkage of the collagenous target tissue.

3. The method of claim 1, further comprising introducing the probe transvaginally.

4. The method of claim 1, wherein the tissue comprises fascia.

5. A method for inhibiting incontinence of a patient, the method comprising:
   introducing a probe into a body of the patient;
   penetrating into one or more tissues of the body with a plurality of tips of the probe; and
   transmitting energy from the probe into the one or more tissues of the body to heat the tissue so that healing of the tissue results in bulking and buttressing of the tissue, and so that the healing-induced bulking and buttressing of the tissue inhibits incontinence.

6. The method of claim 5, further comprising inserting the probe into a urethra of the patient.

7. The method of claim 5, further comprising using a finger inserted into the patient to position the probe.

8. The method of claim 5, wherein the tissue is heated to a temperature in a range from 60 to 110 C.

9. The method of claim 8, wherein the energy comprises an electrical potential, and further comprising controlling the temperature of the tissue by limiting the electrical potential and limiting energy applied to the tissue with a timer coupled to the electrical potential.

10. A method for inhibiting incontinence of a patient, the method comprising:
    introducing a probe into a body of the patient;
    advancing an array of sharpened tips from the probe into a bladder neck and applying an electrical potential to the array;
    transmitting energy from the probe into the bladder neck of the patient body to heat the bladder neck so that the bladder neck inhibits incontinence.

11. The method of claim 10, further comprising using a finger inserted into a vagina of the patient to position the probe.

* * * * *

UNITED STATES PATENT AND TRADEMARK OFFICE
CERTIFICATE OF CORRECTION

PATENT NO. : 7,167,757 B2 Page 1 of 1
APPLICATION NO. : 10/827887
DATED : January 23, 2007
INVENTOR(S) : Frank W. Ingle et al.

It is certified that error appears in the above-identified patent and that said Letters Patent is hereby corrected as shown below:

At Col. 24, line 10, claim 1, please delete "aprobe" and insert --a probe --.

Signed and Sealed this

Fifteenth Day of May, 2007

JON W. DUDAS
*Director of the United States Patent and Trademark Office*